United States Patent [19]

Shiba et al.

[11] 4,144,071
[45] Mar. 13, 1979

[54] PHOTOGRAPHIC LIGHT-SENSITIVE MATERIAL

[75] Inventors: Keisuke Shiba; Toshiaki Aono; Takeshi Hirose; Tadao Shishido, all of Minami-ashigara, Japan

[73] Assignee: Fuji Photo Film Co., Ltd., Minami-ashigara, Japan

[21] Appl. No.: 772,895

[22] Filed: Feb. 28, 1977

Related U.S. Application Data

[63] Continuation of Ser. No. 566,578, Apr. 8, 1975, abandoned.

[51] Int. Cl.² .................. G03C 3/00; G03C 1/06; G03C 1/34
[52] U.S. Cl. .................................. 96/74; 96/95; 96/109
[58] Field of Search .................... 96/74, 95, 109

[56] References Cited

U.S. PATENT DOCUMENTS

| | | | |
|---|---|---|---|
| 2,356,486 | 4/1943 | Weissberger et al. | 96/109 |
| 2,728,661 | 10/1953 | Thirtle et al. | 96/109 |
| 3,379,529 | 4/1968 | Porter et al. | 96/95 |
| 3,620,746 | 11/1971 | Barr | 96/74 |
| 4,015,988 | 4/1977 | Shiba et al. | 96/74 |

OTHER PUBLICATIONS

Stabilization of Photographic Silver Halide Emul. Birr ©1974, Focal Press, N.Y., N.Y., pp. 115-122.

Primary Examiner—J. Travis Brown
Assistant Examiner—L. Falasco
Attorney, Agent, or Firm—Sughrue, Rothwell, Mion, Zinn and Macpeak

[57] ABSTRACT

A silver halide photographic light-sensitive material having improved image quality which comprises at least one hydrophilic colloid layer containing at least one reducing compound, preferably having an oxidation potential less than about 1.5 volts, and at least one compound represented by the following formula (I):

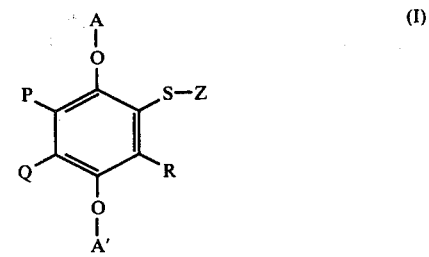

wherein A and A', which may be the same or different, each represents a hydrogen atom or an alkaline-hydrolyzable group, or A' may combine with R or Q to form a ring; and P, Q, and R, which may be the same or different, each represents a hydrogen atom, an alkyl group, an aryl group, a halogen atom, a hydroxyl group, a —Y—W group (wherein Y represents an oxygen atom or a sulfur atom, and W represents an alkyl group, an aryl group, or a heterocyclic group), an —S—Z group (wherein Z represents a heterocyclic group that is substantially photographically inert in the bonded state), or a heterocyclic group; with at least one ballasting group having at least 5 carbon atoms being contained in the molecule.

29 Claims, 2 Drawing Figures

PHOTOGRAPHIC LIGHT-SENSITIVE MATERIAL

This is a Continuation, of application Ser. No. 566,578, filed Apr. 8, 1975 now abandoned.

BACKGROUND OF THE INVENTION

1. Field of the Invention

The present invention relates to a silver halide photographic light-sensitive material having improved image quality and storability, and a method of dispersing the so-called "DIR hydroquinone derivatives".

2. Description of the Prior Art

It is known that image quality can be improved by use of a certain compound that releases a development inhibitor in an image-wise distribution. Examples of such compounds include the so-called "DIR developers" or "DIR hydroquinones" as described, for example, in U.S. Pat. Nos. 3,379,529 and 3,620,746, which may be employed in a silver halide emulsion layer, an interlayer, a filter layer, a protective layer, etc. of a color or black-and-white photographic material. However, hydroquinone derivatives tend to be oxidized by air or the like so that a part of them may release development inhibitors into photographic layers of an unexposed light-sensitive material, or a part of them, if they are present in the material in an oxidized state, may release development inhibitors during the course of development irrespective of the amount of exposure. This results in various disadvantages such as an inhibition of the progress of development, a reduction in sensitivity, a reduction in image density, a gradation unbalance, a deterioration of the storability of the unexposed light-sensitive material, and the like.

SUMMARY OF THE INVENTION

Therefore, an object of the present invention is to provide a photographic light-sensitive material containing a so-called "DIR hydroquinone derivative", which has improved image-quality and good storability as well.

Another object of the present invention is to provide a color photographic light-sensitive material containing a "DIR hydroquinone derivative", which has improved color image-quality and good storability as well.

A further object of the present invention is to provide a method of dispersing "DIR hydroquinone derivatives" into a hydrophilic colloid, in which the oxidation or deterioration of the DIR-hydroquinone derivatives is prevented.

A still further object of the present invention is to provide a fine, granular dispersion of DIR hydroquinone derivatives, which has improved storability.

These and other objects of the present invention are accomplished with a photographic light-sensitive material, particularly a color photosensitive material, comprising at least one hydrophilic colloid layer containing at least one reducing compound having an oxidizing potential less than about 1.5 volts and at least one compound represented by the general formula (I)

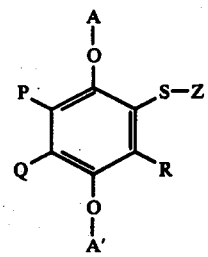

wherein A and A' each represents a hydrogen atom or an alkaline-hydrolyzable group, or A' may combine with R or Q to form a ring; and P, Q, and R each represents a hydrogen atom, an alkyl group, a halogen atom, a hydroxyl group, a —Y—W group, wherein Y represents an oxygen atom or a sulfur atom and W represents an alkyl group, an aryl group, or a heterocyclic group wherein Z represents a heterocyclic group which is substantially photographically inert in the bonded state; with at least one ballasting group having at least 5 carbon atoms being contained in the molecule, and, more particularly, with a photosensitive material, particularly a color photosensitive material, comprising at least one hydrophilic colloid layer containing a dispersion prepared by dispersing into a hydrophilic colloid solution DIR hydroquinone derivatives, particularly those represented by the general formula (I) in the presence of at least one reducing compound having an oxidizing potential of less than about 1.5 volts, preferably from 0.5 to 1.5 volts.

DETAILED DESCRIPTION OF THE INVENTION

Figure 1:
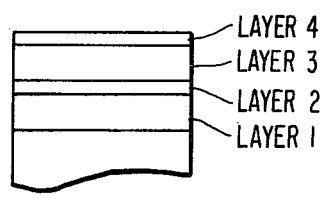
FIG. 1 and FIG. 2 each illustrates the layer arrangement of an embodiment of the light-sensitive material of the invention.
Figure 2:
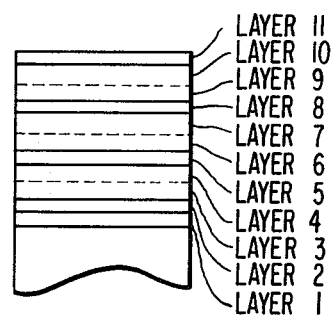

As described above, the photographic light-sensitive material of this invention contains a compound of a general formula (I)

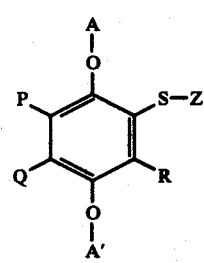

wherein A and A' each represents a hydrogen atom or an alkaline-hydrolyzable group (e.g., alkylcarbonyl, alkoxycarbonyl, alkyloxycarbonylcarbonyl, etc., in which the alkyl moieties of each of these groups can contain 1 to 15 carbon atoms), or A' may combine with R or Q to form a ring (e.g., oxathiazole, etc.); and P, Q, and R each represents a hydrogen atom, an alkyl group (e.g., having 1 to 32 carbon atoms such as methyl, ethyl, octyl, tertoctyl, dodecyl, pentadecyl, octadecyl, etc.), a halogen atom (e.g., chlorine, bromine, etc.), a hydroxyl group, a —Y—W group (wherein Y represents an oxygen atom or a sulfur atom and W represents an alkyl group (e.g., having 1 to 18 carbon atoms such as 2- hydroxyethyl, ethoxycarbonylmethyl, 2-ethylhexyl, n-dodecyl, n-hexadecyl, n-octadecyl, etc.), an aryl group (e.g., phenyl, tolyl, etc.) or a heterocyclic group (e.g., tetrazolyl, thiazolyl, quinonyl, etc.), an —S—Z group (wherein Z represents a heterocyclic group which is substantially photographically inert in the bonded state), or a heterocyclic group (e.g., thiazolyl, oxazolyl, benzothiazolyl, imidazolyl, etc.); with at least one ballasting group having at least 5 carbon atoms being contained in the molecule. The above-described alkyl groups can also be substituted with substituents such as a halogen atom (e.g., fluorine, bromine, chlorine, etc.), a hydroxyl group, an alkoxy group (e.g., methoxy, ethoxy, ethoxyethoxy, hexyloxy, dodecyloxy, etc.), an aryloxy group (e.g., phenoxy, p-tert-butyl-phenoxy, etc.), an aryl group (e.g., phenyl, tolyl, p-tridecanamidophenyl, naphthyl, etc.), an amino group (e.g., ethylamino, dodecylamino, di-ethylamino, N-methyl-N-dodecylamino, anilino, toluidino, phenethylamino, etc.), an acylamino group (e.g., formamido, acetamido, pivaloylamido, lauroylamido, stearoylamido, benzoylamido, etc.), an imido group, a carboxy group, an alkoxycarbonyl group (e.g., ethoxycarbonyl, dodecyloxycarbonyl, etc.), a carbamoyl group (e.g., tert-butylcarbamyl, di-ethylcarbamyl, iso-octylcarbamyl, tolylcarbamyl, etc.) or a sulfonamido group. These substituents can be further substituted.

Of the DIR-hydroquinone derivatives which can be used in the present invention, preferred DIR-hydroquinone derivatives are represented by general formula (Ia)

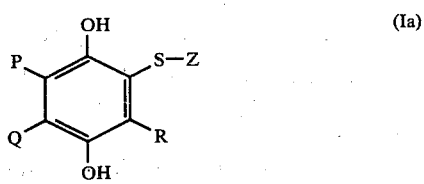

wherein P, Q, R, and Z each have the same meanings as defined in general formula (I) above with at least one of P, Q, and R being a —Y—W group wherein Y and W each have the same meanings as defined in general formula (I), and with at least one of P, Q, or R containing a ballasting group.

The photographically inert heterocyclic groups represented by Z in general formula (I) and (Ia) include, for example, a tetrazolyl group (e.g., 1-phenyltetrazolyl, etc.), a triazoyl group (e.g., 4-phenyl-1,2,4-triazol-5-yl, 3-n-pentyl-4-phenyl-1,2,4-triazol-5-yl, etc.), a thiadiazolyl group (e.g., 2-methylthio-1,3,4-thiadiazol-5-yl, 2-amino-1,3,4-thiadiazol-5-yl, etc.), an oxadiazolyl group (e.g., 2-pentyl-1,3,4-oxadiazol-5-yl, etc.), a tetraazaindenyl group (e.g., 6-methyl-1,3,3a,7-tetraazainden-4-yl, 6-n-nonyl-1,3,3a,7-tetraazainden-4-yl, etc.), an oxazolyl group (e.g., benzoxazol-2-yl, etc.), a thiazolyl group (e.g., benzothiazol-2-yl, etc.), and the like.

The ballasting group introduced into the DIR hydroquinone derivatives used in the present invention contains at least 5 carbon atoms, preferably from 5 to about 32 carbon atoms. Aliphatic groups that contain from 5 to 32 carbons are particularly preferred as the ballasting group.

Of the DIR hydroquinone derivatives used in the present invention, particularly preferred DIR hydroquinone derivatives are represented by general formula (Ib)

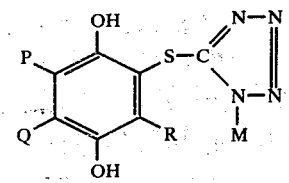

wherein P, Q, and R each represents a hydrogen atom, an alkyl group (e.g., methyl, ethyl, 1,1,3,3-tetramethylbutyl, n-pentadecyl, 2-propenyl, etc.), an aryl group (e.g., phenyl, p-tolyl, o-carboxyphenyl, o-methoxycarbonylphenyl, p-methoxyphenyl, etc.), a halogen atom (e.g., chlorine, iodine, etc.), a —Y—W group wherein Y represents an oxygen atom or a sulfur atom, and W represents an alkyl group (e.g., 2-ethylhexyl, n-dodecyl, n-hexadecyl, n-octadecyl, hydroxylcarbonylmethyl, ethoxycarbonylmethyl, 2-hydroxyethyl, etc.), an aryl group (e.g., phenyl, p-tolyl, o-tolyl, o-methoxy, carboxyphenyl, etc.), an alkoxy or aryloxy group (e.g., methoxy, phenoxy, o-octadecyloxycarbonylphenoxy, etc.), a heterocyclic group (e.g., 2-benzotriazolyl, 2-imidazolyl, etc.)), or a heterocyclic group and M represents a phenyl group, a substituted phenyl group (e.g., tolyl, xylyl, acetaminophenyl, etc.), or a lower alkyl group, (e.g., having 1 to 4 carbon atoms such as methyl, ethyl, propyl, butyl, etc.).

An important feature of the DIR hydroquinone derivatives of the invention is that the reducing power, or DIR-activity, of the hydroquinone derivatives tends to be increased by the introduction of the —Y—W groups (preferably those in which W represents an alkyl or aryl group), whereas their reducing power, or DIR-activity, generally tends to be reduced by the introduction of the —S—Z group. Another important feature of the DIR hydroquinone derivatives of this invention is that, when an aliphatic group having at least 5 carbon atoms is present as the ballasting group, preferably in the -W group of the molecule, not only is the molecule rendered nondiffusible, but the co-called "abnormal color-formation" can be prevented. The term "abnormal color-formation" refers to the phenomenon where the image formed by color development using a primary aromatic amine as a developer is stained blue by the blue dyes by-produced from DIR hydroquinones. The abnormal color-formation can also be prevented by use of the DIR-hydroquinone derivatives of the invention in which Q is other than a hydrogen atom or those which have a substituent in the 4- or 5-position of the hydroquinone per se. Still a further future of the DIR hydroquinone derivatives of the invention is that they can be prepared without much difficulty. Other features will be understood from the description described herein.

Some examples of the DIR-hydroquinone derivatives of the general formula (I) of the invention are shown below.

Compound I-1:
  2-n-Dodecylthio-5-(1'-phenyltetrazol-5'-ylthio)hydroquinone

Compound I-2:
  2-n-Octadecylthio-5-(1'-phenyltetrazol-5-ylthio)hydroquinone

Compound I-3:
  2-n-Hexadecylthio-5-(1'-phenyltetrazol-5-ylthio)hydroquinone

Compound I-4:

2-2′,5′-Dihydroxy-6′-(1″-phenyltetrazol-5″-ylthio)-4′-(1‴,1‴,3‴,3‴-tetramethylbutyl) phenylthiobenzoic acid Compound I-5:
2-[2′,5′-Dihydroxy-6′-(1″-phenyltetrazol-5″-ylthio)-3′-(1‴,1‴,3‴,3‴-tetramethylbutyl)]phenylthiobenzoic acid Compound I-6:
2-(1′-Phenyltetrazol-5′-ylthio)-3-phenylthio-6-(1″,1″,3″,3″-tetramethylbutyl)hydroquinone Compound I-7:
2-(1′-Phenyltetrazol-5′-ylthio)-3-phenylthio-5-(1″,1″,3″,3″-tetramethylbutyl)hydroquinone Compound I-8:
2,5-Dihydroxy-6-(1′-phenyltetrazol-5′-ylthio)-4-(1″,1″,3″,3″-tetramethylbutyl)phenylthioacetic acid Compound I-9:
2-(2′,5′-Dihydroxy-3′-n-hexadecylthio-6′-(1″-phenyltetrazol-5″-ylthio)]phenylthiobenzoic acid Compound I-10:
2-n-Hexadecylthio-5-(1′-phenyltetrazol-5′-ylthio)-6-phenylthiohydroquinone Compound I-11:
4-(1′-Phenyltetrazol-5′-ylthio)-5-hydroxy-7-(1″,3″,3″,3″-tetramethylbutyl)benzoxathiol-2-one Compound I-12:
2-[2′,5′-Dihydroxy-6′-(1″-phenyltetrazol-5″-ylthio)-3′-(1‴,1‴,3‴,3‴-tetramethylbutyl)]phenylthiobenzoic acid methyl ester Compound I-13:
2-[2′,5′-Dihydroxy-6′-(1″-phenyltetrazol-5″-ylthio)-4′-(1‴,1‴,3‴,3‴-tetramethylbutyl)]phenylthiobenzoic acid methyl ester Compound I-14:
2-[2′,5′-Dihydroxy-3′-n-pentadecylthio-6′-(1″-phenyltetrazol-5″-ylthio)]phenylthiobenzoic acid methyl ester Compound I-15:
2-n-Octyloxycarbonylmethylthio-6-phenyl-3-(1′-phenyltetrazol-5′-ylthio)hydroquinone Compound I-16:
2-p-Nitrophenylthio-3-(1′-phenyltetrazol-5′-ylthio)-6-(1″,1″,3″,3″-tetramethylbutyl)hydroquinone Compound I-17:
2-(2′-Methylthio-1′,3′,4′-thiadiazol-5′-ylthio)-6-(1″,1″,3″,3″-tetramethylbutyl)hydroquinone Compound I-18:
3-(2′-Methylthio-1′,3′,4′-thiadiazol-5′-ylthio)-6-(1″,1″,3″,3″-tetramethylbutyl)hydroquinone Compound I-19:
2,3-bis(2′-Methylthio-1′,3′,4′-thiadiazol-5-ylthio)-6-(1″,1″,3″,3″-tetramethylbutyl)hydroquinone Compound I-20:
2-(3′-n-Pentyl-4′-phenyl-1′,2′,4′-triazol-5′-ylthio)-5-(1″,1″,3″,3″-tetramethylbutyl)hydroquinone Compound I-21:
2-(6′-Methyl-1′,3′,3a′,7′-tetrazainden-4′-ylthio)-6-(1″,1″,3″,3″-tetramethylbutyl)hydroquinone Compound I-22:
2,3-bis(6′-Methyl-1′,3′,3a′,7′-tetrazainden-4′-ylthio)-6-(1″,1″,3″,3″-tetramethylbutyl)hydroquinone Compound I-23:
2-n-Hexadecylthio-5-(2′-methylthio-1′,3′,4′-thiadiazol-5′-ylthio)hydroquinone Compound I-24:
2-[2′,5′-Dihydroxy-6′-(2″-methylthio-1″,3″,4″-thiadiazol-5″-ylthio)-3′-(1‴,1‴,3‴,3‴-tetramethylbutyl)]-phenylthiobanzoic acid Compound I-25:
2-(2′-Amino-1′,3′,4′-thiadiazol-5′-ylthio-5-(1″,1″,3″,3″-tetramethylbutyl)hydroquinone Compound I-26:
2-[2′,5′-Dihydroxy-6′-(2″-amino-1″,3″,4″-thiadiazol-5″-ylthio)-4′-(1‴,1‴,3‴,3‴-tetramethylbutyl)]phenylthiobenzoic acid Compound I-27:
2-(2′-Amino-1′,3′,4′-thiadiazol-5′-ylthio)-3-n-dodecylthio-6-(1″,1″,3″,3″-tetramethylbutyl)hydroquinone Compound I-28:
2-(6′-t-Butyl-1,3,3a,7-tetrazaindene-4-ylthio)-6-(1″,1″,3″,3″-tetramethylbutyl)hydroquinone Compound I-29:
2-(6′-n-Nonyl-1′,3′,3a′,7′-tetrazainden-4′-ylthio)-6-(1″,1″,3″,3″-tetramethylbutyl)hydroquinone Compound I-30:
2-(4′-Phenyl-1′,2′,4′-triazol-5′-ylthio)-5-(1″,1″,3″,3″-tetramethylbutyl)hydroquinone Compound I-31:
2-(2′-Phenyl-1′,3′,4′-oxadiazol-5′-ylthio)-5-(1″,1″,3″,3″-tetramethylbutyl)hydroquinone Compound I-32:
2-(1′-Phenyltetrazol-5′-ylthio)-5-n-octyloxycarbonylmethylthiohydroquinone Compound I-33:
2-t-Dodecylthio-5-(1′-phenyltetrazol-5′-ylthio)-hydroquinone Compound I-34:
2-(Benzoxazol-2′-ylthio)-5-n-octadecylhydroquinone Compound I-35:
2-(2′-Methylphenylthio)-6-n-octadecylthio-3-(1′-phenyltetrazol-5″-ylthio)hydroquinone Compound I-36:
2-n-Octyloxycarbonylmethylthio-3-(1′-phenyltetrazol-5′-ylthio)-6-p-tolylhydroquinone Compound I-37:
2-Ethoxycarbonylmethylthio-6-n-hexadecylthio-3-(1′-phenyltetrazol-5′-ylthio)hydroquinone Compound I-38:
2-Phenylthio-3-(1′-phenyltetrazol-5′-ylthio)-5-n-dodecylthiohydroquinone Compound I-39:
2-t-Octyl-5-(1′-phenyltetrazol-5′-ylthio)hydroquinone Compound I-40:
2-t-Octyl-6-(1′-phenyltetrazol-5′-ylthio)hydroquinone Compound I-41:
2-n-Pentadecyl-5-(1′-phenyltetrazol-5′-ylthio)-hydroquinone Compound I-42:
2-n-Octadecylthio-(X),(X′)-bis-(1′-phenyltetrazol-5′-ylthio)hydroquinone Compound I-43:
2-(4′-Methylphenyl)-(X)-(1′-phenyltetrazol-5′-ylthio)-hydroquinone Compound I-44:
2-t-Octyl-6-(2′-methylthio-1′,3′,4′-thiadiazol-5′-ylthio)-hydroquinone Compound I-45:
2-n-Pentadecyl-5-(2′-methylthio-1′,3′,4′-thiadiazol-5′-ylthio)hydroquinone Compound I-46:
2-t-Octyl-5-(2′-amino-1′,3′,4′-thiadiazol-5′-ylthio)-hydroquinone Compound I-47:

2-n-Hexadecylthio-5-(2'-methylthio-1',3',4'-thiadiazol-5'-ylthio)hydroquinone

Compound I-48:

2-t-Octyl-5-(2'-n-pentyl-1'-phenyl-1',3',4'-triazol-5'-ylthio)hydroquinone

The DIR-hydroquinone derivatives used in the present invention can be prepared by the addition reaction of mercapto compounds to benzoquinones as described in U.S. Pat. No. 3,379,529.

Representative methods of their preparation are illustrated below. Unless otherwise indicated herein, all parts, percents, ratios and the like are by weight.

Preparation 1 (Compound I-3)

2-n-Hexadecylthio-p-benzoquinone (315 g) was added to methanol (1 liter), and the mixture was stirred in an ice bath. To this mixture a solution of 1-phenyl-5-mercaptotetrazole (155 g) in methanol (800 ml) was added dropwise. After the addition was over, the resulting mixture was stirred for 3 hours in an ice bath and for 8 hours at room temperature (i.e., about 20°–30° C.) to precipitate crystals.

The crystals formed were filtered off, and recrystallized from benzene. 350 g of 2-n-hexadecylthio-5-(1'-phenyltetrazol-5-ylthio)hydroquinone was obtained; M.P. 129° to 131° C.

Preparation 2 (Compound I-6)

2-(1'-Phenyltetrazol-5-ylthio)-6-(1'',1'',3'',3''-tetramethylbutyl)-p-benzoquinone (15 g) was added to methanol (150 ml). To this mixture a solution of thiophenol (4.5 g) in methanol (25 ml) was added. After the addition was over, the resulting mixture was stirred in an ice bath. The crystals formed were filtered off, and recrystallized from a mixed solution of hexane and ethyl acetate.

2-(1'-Phenyltetrazol-5'-ylthio)-3-phenylthio-6-(1'',1'',3'',3''-tetramethylbutyl)hydroquinone (7.5 g) was obtained; M.P. 147° C.

Preparation 3 (Compound I-20)

3-Mercapto-5-n-benzyl-4-phenyl-1,2,4-triazole (13 g) was dissolved in methanol (200 ml), and the solution was stirred in an ice bath. To this solution 2-(1',1',3',3'-tetramethylbutyl)-p-benzoquinone (12 g) was added dropwise. After the addition was over, the resulting mixture was stirred for 2 hours in an ice bath, allowed to stand overnight, and concentrated under reduced pressure. Diethyl ether was added to the residue, the crystals precipitated were filtered off, and the crystals recrystallized frm ethyl acetate.

2-(3-n-Pentyl-4'-phenyl-1,2,4-triazole-5'-ylthio)-5-(1'',1'',3'',3''-tetramethylbutyl)hydroquinone (5 g) was obtained; M.P. 198° C.

The DIR hydroquinone derivatives of the general formula I according to the present invention, particularly those represented by general formula (Ib), have strong DIR-activities. On the other hand, they tend to be oxidized, particularly when they are dissolved in a solvent such as ethyl acetate, ethyl butyrate, acetone, ethoxyethoxyethyl acetate, tricresyl phosphate, dibutyl phthalate, acetyl tributyl citrate, etc., to form a dispersion thereof. The quinones produced by the oxidation of the DIR hydroquinone derivatives have extremely low solubility, tend to become nuclei for deposits generated in dispersions, and cause desensitization. However, these defects can be removed by the presence of the reducing compounds in accordance with the invention.

After the addition of the DIR hydroquinone derivatives of the invention to a melted emulsion, the emulsion is preferably coated on a support as soon as possible. Thereby, the storability of the light-sensitive materials prepared can be improved and the deterioration in the photographic properties (i.e., sensitivity, gradation, fogging, etc.) of a light-sensitive material, which is caused by the coexistence of the DIR-hydroquinone derivatives with silver halide grains, can be prevented.

The reducing compounds used in the present invention preferably have an oxidizing potential less than about 1.5 volts, more preferably from 1.5 to 0.5 volt, especially preferably from 1.2 to 0.7 volt. The oxidation potential ($E_{ox}$) can be measured easily by those skilled in the art. Methods for measuring oxidation potentials are described in A. Stanienda, Naturwissenschaften, Vol. 47, p. 353 and p. 512 (1960), P. Delahay, New Instrumental Methods in Electrochemistry, Interscience Publishers (1960), L. Meits, Polarographic Techniques, Vol. 2, ibid. (1965), and the like. $E_{ox}$ values are determined on a $1 \times 10^{-4}$ to $1 \times 10^{-6}$ mole acetonitrile solution containing sodium perchlorate as the supporting electrolyte using a rotating platinum electrode and a saturated calomel electrode as a reference electrode. The measured values include errors up to 100 mV. due to the influence of the liquid-junction potential difference, the imperfections in correction of the liquid resistence in the sample solution, etc., and the like. The reproducibility of the value can be assured by the addition of a standard sample as a control. The $E_{ox}$ value is the potential difference required to transfer at the anode an electron occupying the highest energy level from a reducing compound to be measured to the electrode, that is to say, the $E_{ox}$ value is a measure of the reducibility of a compound.

The reducing compounds used in the invention can be either an inorganic compound or an organic compound, and can be selected from compounds which are generally referred to as antioxidants. Of these compounds, phenol derivatives, particularly dihydroxybenzene derivatives, e.g., pyrocatechols and tocophenols, and trihydroxybenzene derivatives, e.g., pyrogallols, etc., naphthol derivatives, particularly dihydroxynaphthalene derivatives, trihydroxynaphthalene derivatives, etc., ascorbic acid derivatives, reductones, aromatic amino compounds, hydroxyamino compounds, stannous salts, dithio compounds, and the like are useful. Watersoluble reducing compounds used in the invention can be added to a colloidal solution of the DIR hydroquinone derivatives in the form of an aqueous solution thereof. Oil-soluble reducing compounds used in the invention can be employed together with the DIR hydroquinone derivatives by dissolving them in an organic solvent, as a dispersion medium. The reducing compounds used in the invention can also be admixed with the DIR hydroquinone derivatives during the preparation or before the dispersion of the DIR hydroquinones derivatives.

The reducing compounds used in the present invention can be selected from the compounds as described in U.S. Pat. Nos. 2,360,290; 2,418,613; 2,675,314; 2,701,197; 2,704,713; 2,728,659; 2,732,300; 2,735,765; 2,710,801; 2,816,082; 3,457,079; 3,069,262; 2,735,765; 3,432,300; 3,573,050; 3,574,627; 3,698,909 and 3,764,337; Japanese Patent Publication No. 13496/68 and the like.

The reducing compounds used in the invention can also be selected from the compounds as described in Gerald Scott, Atmospheric Oxidation and Autooxidants, Elsevier Publishing Company (1965), and N. M. Emanuel and Yun. Lyaskovskaya, translated by K. A.

Allen, The Inhibition of Fat Oxidation Process, Pergamon Press (1967).

As described above, the reducing compounds used in the present invention preferably have an oxidation potential less than about 1.5 volts. However, the reducing compounds can be temporarily protected by an alkaline hydrolyzable group.

As reducing compounds used in the present invention, phenol derivatives having one or two aliphatic groups containing not less than 8 carbon atoms represented by general formula (II) below are particularly useful:

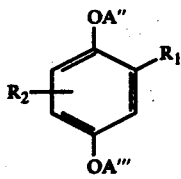
(II)

wherein $R_1$ represents a hydrogen atom or a straight-chain or branched alkyl group containing from 8 to 20 carbon atoms (e.g., n-octyl, t-octyl, n-decyl, n-dodecyl, 1-methylundecyl, n-pentadecyl, 1-methylpentadecyl, n-octadecyl, etc.); $R_2$ represents an hydrogen atom or a straight-chain or branched alkyl group containing from 8 to 20 carbon atoms (e.g., n-octyl, t-octyl, n-decyl, n-dodecyl, 1-methylundecyl, n-pentadecyl, 1-methylpentadecyl, n-octadecyl, etc.); A" and A''' each represents a hydrogen atom or an alkaline hydrolyzable group (e.g., alkylcarbonyl, alkoxycarbonyl, alkyloxycarbonylcarbonyl, etc. in which the alkyl moieties of each of these groups can contain 1 to 15 carbon atoms), and the benzene ring may be additionally substituted with an alkyl group containing 1 to 8 carbon atoms (e.g., methyl, ethyl, n-butyl, t-butyl, amyl, iso-amyl, n-hexyl, n-octyl, t-octyl, etc.), a halogen atom (e.g., fluorine, chlorine, bromine, etc.), an aryl group (e.g., phenyl, tolyl, methoxyphenyl, chlorophenyl, naphthyl), a hydroxyl group, a heterocyclic group (e.g., thiazolyl, oxazolyl, benzothiazolyl, imidazolyl, etc.), and the like. The alkyl group represented by $R_1$ and $R_2$ can also be substituted with substituents such as a halogen atom (e.g., fluorine, bromine, chlorine, etc.), a hydroxyl group, an alkoxy group (e.g., methoxy, ethoxy, ethoxyethoxy, hexyloxy, dodecyloxy, etc.), an aryloxy group (e.g., phenoxy, p-tert-butylphenoxy, etc.), an aryl group (e.g., phenyl, tolyl, p-tridecanamidophenyl, naphthyl, etc.), an amino group (e.g., ethylamino, dodecylamino, di-ethylamino, N-methyl-N-dodecylamino, anilino, toluidino, phenethylamino, etc.), an acylamino group (e.g., formamido, acetamido, pivaloylamido, lauroylamido, stearoylamido, benzoylamido, etc.), an imido group, a carboxy group, an alkoxycarbonyl group (e.g., ethoxycarbonyl, dodecyloxycarbonyl, etc.), a carbamoyl group (e.g., tert-butylcarbamyl, diethylcarbamyl, iso-octylcarbamyl, tolylcarbamyl, etc.) or a sulfonamido group. These substituents can be futher substituted.

Some of these compounds are described, for example, in U.S. Pat. Nos. 2,336,327; 2,728,659; 2,835,579; and 3,700,453; and the like.

Specific examples of suitable reducing compounds are shown below:
Compound R-1:
  2,5-Di-tert-octylhydroquinone
Compound R-2:
  2-n-Octadecylthiohydroquinone
Compound R-3:
  2-n-Hexadecylhydroquinone
Compound R-4:
  2-n-Octadecylthio-5-tert-octylhydroquinone
Compound R-5:
  Hydroquinone
Compound R-6:
  2-(3'-Methylphenyl)hydroquinone
Compound R-7:
  Ascorbic acid
Compound R-8:
  Ascorbic palmitate
Compound R-9:
  2,3-Dihydroxynaphthalene
Compound R-10:
  7,7'-Dimethyl-6,6'-dihydroxy-4,4,4',4'-tetramethyl-bis-2,2'-spirochroman
Compound R-11:
  2,3,5-Trimethylhydroquinone
Compound R-12:
  Sodium bisulfite
Compound R-13:
  N-Methyl-N-($\beta$-methylsulfonamidoethyl)-p-aminophenol
Compound R-14:
  Hydroxylamine
Compound R-15:
  Pyrogallol
Compound R-16:
  Gallic acid
Compound R-17:
  Diaminodurene The DIR hydroquinone derivative(s) used in the present invention can be dissolved in an organic solvent, such as tricresyl phosphate, dibutyl phthalate, a fatty oil which is liquid at ordinary temperature (e.g., 20°–30° C.), e.g., acetyl-tri(2-ethylhexyl)citrate, tributyl glycerol, N,N-diethylcapramide, etc., and dispersed in a hydrophilic colloid solution in the presence of the reducing compound(s). Hydrophobic or oil-soluble reducing compounds, for example, Compounds R-1, R-2, R-3, R-4, R-8, R-9, R-10, R-11, etc. can be incorporated by dissolving them in a high boiling solvent. Water-soluble reducing compounds, for example, Compounds R-5, R-6, R-7, R-12, etc. can be incorporated directly in a hydrophilic colloid used as a disperse medium.

The amount of the reducing compounds, preferably the hydroquinone derivatives represented by general formula (II), employed together with the DIR hydroquinones is not critical, but it is preferably from about 1 to 70 mol%, particularly preferably from 10 to 60 mol%, based on the total moles of the reducing compound and the DIR hydroquinone derivatives of the general formula (I).

The DIR hydroquinone derivatives and/or the reducing compounds, particularly the hydroquinone derivatives represented by general formula (II), can be incorporated in an emulsion using a method for incorporating a coupler in an emulsion with or without preparing a dispersion thereof. In case of color light-sensitive materials, the proportion of the DIR hydroquinone derivatives of general formula (I) which are used in the invention can be less than 50 mol%, preferably from 30 to 1 mol%, based on the moles of the coupler used. After the emulsion of the DIR hydroquinone derivatives of the invention is incorporated in a silver halide emulsion, the silver halide emulsion is preferably coated onto a support substantially immediately. The dispersion of the DIR-hydroquinone derivatives can be prepared by dissolving them in a high boiling organic solvent such as tricresyl phosphate, dibutyl phosphate, a fatty oil which is a liquid at ordinary temperature, e.g., acetyl-tri(2-ethylhexyl)citrate, tributyl glycerol, etc., waxes, higher fatty acids and their esters, N-n-butyl-acetanilide, N,N-diethylcapramide, and the like, and then dispersing the solution into a hydrophilic colloid solution such as gelatin, according to a method as described, for example, in U.S. Pat. Nos. 2,304,939; 2,322,027; 2,801,170; 2,801,171; 2,949,360 and German Pat. No. 1,143,70. They can be added according the method as described in U.S. Pat. No. 3,379,529. They can also be dispersed into a hydrophilic colloid solution such as gelatin by using a synthetic polymer together with the organic solvent.

The oxidation or change in quality of the DIR hydroquinone compounds can be prevented more effectively by incorporating at least one organic acid, particularly those containing at least one carboxyl group, such as citric acid, tartaric acid, fumaric acid, succinic acid, salicylic acid, phthalic acid, polyacrylic acid, glycolic acid, ethylenediaminetetraacetic acid, etc., or the esters (e.g., preferably the alkyl esters having 1 to 12 carbon atoms in the alkyl moieties thereof) or salts (e.g., alkali metal such as sodium, potassium, etc., ammonium, trimethylammonium, etc.) thereof, into a high boiling organic solvent and/or a hydrophilic colloid solution together with the DIR hydroquinone derivatives and-/or the reducing compounds, particularly the hydroquinone derivatives represented by general formula (II).

The mean particle size of the dispersion used in the invention can vary over a wide range, but the mean particle size is preferably from about 0.05 to $2\mu$, more preferably from 0.05 to $0.5\mu$.

Examples of hydrophilic protective colloids which can be used in a hydrophilic protective colloid layer and a hydrophilic colloid solution in accordance with the invention, include, in addition to gelatin, colloidal albumin, casein, cellulose derivatives such as carboxymethyl cellulose, hydroxyethyl cellulose, etc., saccharide derivatives such as agar-agar, sodium alignate, starch derivatives, etc., synthetic hydrophilic colloids such as polyvinyl alcohol, poly-N-vinylpyrolidone, polyacrylic acid copolymers, polyacrylamide, or derivatives and partially-hydrolyzed products thereof. If desired, a compatible mixture of two or more of these colloids can be employed. Of these colloids, gelatin is most commonly employed, but the gelatin can be replaced, partially or completely, by a so-called gelatin derivative, i.e., gelatin treated with or modified by a compound containing a group capable of reacting with the amino, imino, hydroxy, or carboxy functional groups contained in gelatin molecules, or a gelatin graft polymer, i.e., gelatin to which other polymeric chains are grafted, as well as synthetic polymers.

Examples of compounds which can be used for the preparation of the gelatin derivatives described above, are the isocyanates, acid chlorides, and acid anhydrides as described in U.S. Pat. No. 2,614,928; the acid anhydrides as described in U.S. Pat. No. 3,118,766; the bromoacetic acids as described in Japanese Patent Publication No. 5514/64; the phenyl glycidyl ethers as described in Japanese Patent Publication No. 26845/67; the vinylsulfones as described in U.S. Pat. No. 3,132,945; the N-allylvinylsulfones as described in British Pat. No. 861,414; the maleinamides as described in U.S. Pat. No. 3,136,846; the acrylonitriles as described in U.S. Pat. No. 2,594,293; the polyalkylene oxides as described in U.S. Pat. No. 3,312,553; the epoxy compounds as described in Japanese Patent Publication No. 26845/67; the acid esters as described in U.S. Pat. No. 2,762,639; the alkane sultones as described in British Pat. No. 1,033,189; and the like.

As graft polymers to be grafted to gelatin, a variety of polymers or copolymers prepared from monomers such as acrylic acid, methacrylic acid, or the ester, amide, or nitrile derivatives thereof, etc., or styrene, which are generally referred to as a vinyl monomer, can be used. A number of examples of these polymers or copolymers are described, for example, in U.S. Pat. Nos. 2,763,625; 2,831,767 and 2,956,883; Polymer Letters, 5, 595 (1967); Phot. Sci. Eng., 9, 148 (1965); and J. Polymer Sci., A-1, 9, 3199 (1971). Of these compounds, hydrophilic vinyl polymers which are compatible with gelatin to some extent, for example, polymers or copolymers of acrylamide, methacrylamide, hydroxyalkylacrylamide, hydroxymethacrylamide, etc. are particularly preferable.

Examples of hydrophilic colloid layers which can contain the dispersions in accordance with the invention include subsidiary layers such as a protective layer, an anti-halation layer, an interlayer, a filter layer, an anti-irradiation layer, and a development contamination-preventing layer, as well as the light-sensitive silver halide emulsion layer.

Color photographic materials in accordance with the invention can contain a coupler. Examples of useful couplers which can be used in the present invention include 4- and 2-equivalent couplers, particularly those yellow color forming couplers represented by the following general formula (III):

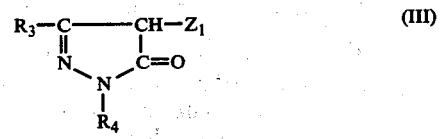

wherein $R_3$ represents a primary, secondary, or tertiary alkyl group (e.g., methyl, propyl, n-butyl, tert-butyl, hexyl, 2-hydroxyethyl, 2-phenylethyl, pentadecyl, etc.), an aryl group (e.g., phenyl, 2,4-di-tert-phenyl, etc.), an alkoxyl group (e.g., methoxy, ethoxy, benzyloxy, etc.), an aryloxy group (e.g., phenoxy, etc.), a heterocyclic group (e.g., quinolinyl, pyridyl, benzofuranyl, oxazolyl, etc.), an amino group (e.g., methylamino, diethylamino, phenylamino, tolylamino, 4-(3-sulfobenzamino)anilino, 2-chloro-5-acylaminoanilino, 2-chloro-5-alkoxycarbonylanilino, 2-trifluoromethylamino, etc.), an acylamino group (e.g., alkylcarbamido such as ethylcarbamido, arylcarbamido, heterocyclic carbamido such as benzothiazolylcarbamido, sulfoamido, heterocyclic sulfoamido, etc.), an ureido group (e.g., alkylureido, arylureido, heterocyclic ureido, etc.), and the like; $R_4$ represents an aryl group (e.g., naphthyl, phenyl, 2,4,6-trichlorophenyl, 2-chloro-4,6-dimethylphenyl, 2,6-dichloro-4-methoxyphenyl, 4-methylphenyl, 4-acylaminophenyl, 4-alkylaminophenyl, 4-trifluoromethylphenyl, 3,5-dibromophenyl, etc.), a heterocyclic group (e.g., benzofuranyl, benzothiazolyl, quinolinyl, etc.), an alkyl group (e.g., methyl, t-butyl, benzyl, etc.), and the like; and $Z_1$ represents a hydrogen atom or a group capable of being released upon color development, for example, a thiocyano group, an acyloxy group, an alkoxyl group, an alkoxycarbonyloxy group, an aryloxycarbonyloxy group, a disubstituted amino group, an arylazo group, a heterocyclic azo group, etc., as described, for example, in U.S. Pat. Nos. 3,419,319; 3,252,924; 3,311,476 and 3,227,550; U.S. Pat. 3,926,631, filed April 15, 1974 and U.S. Patent Application 471,639, filed May 20, 1974 now abandoned and the like; those magenta forming couplers represented by the general formula (IV)

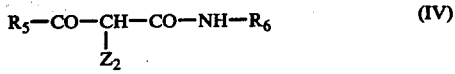

wherein $R_5$ represents a primary, secondary, or tertiary alkyl group (e.g., tert-butyl, 1,1-dimethylpropyl, 1,1-dimethyl-1-methoxyphenoxymethyl, 1,1-dimethyl-1-ethylthiomethyl, etc.), an aryl group (e.g., phenyl, alkylphenyl such as 2-methylphenyl, 3-octadecylphenyl, etc., alkoxyphenyl such as 2-methoxyphenyl, 4-methoxyphenyl, etc., halogenated phenyl, 2-chloro-5-alkylcarbamidophenyl, 2-chloro-5-[α-(2,4-di-tert-aminophenoxy)butyramido]phenyl, 2-methoxy-5-alkylamidophenyl, 2-chloro-5-sulfoamidophenyl, etc.); $R_6$ represents a phenyl group (e.g., 2-chlorophenyl, 2-halo-5-alkylamidophenyl, 2-chloro-5-[α-(2,4-di-tert-amylphenoxy)-acetamido]phenyl, 2-chloro-5-(4-methylphenylsulfoamido)phenyl, 2-methoxy-5-(2,4-di-tert-amylphenoxy)acetamidophenol, etc.); and $Z_2$ represents a hydrogen atom or a group capable of being released upon color development, for example, a halogen atom, an acyloxy group, an aryloxy group, a heterocyclic carbonyloxy group, a sulfimido group, an alkylsulfoxy group, an arylsulfoxy group, a phthalimido group, a dioxoimidazolidinyl group, a dioxooxazolidinyl group, a dioxothiazolidinyl group, a dioxomorpholinyl group, etc., as described, for example, in U.S. Pat. Nos. 3,227,550; 3,253,924; 3,277,155; 3,265,506; 3,408,194 and 3,415,652; French Pat. No. 1,411,384; British Pat. 944,490; 1,040,710 and 1,118,028; German Patent application (OLS) Nos. 2,056,941; 2,163,812; 2,213,461 and 2,219,917; U.S. Pat. 4,012,259, filed May 14, 1974, and the like; and cyan forming couplers represented by the general formulas (V) and (VI)

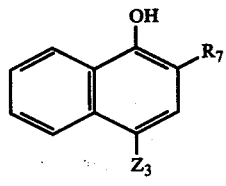

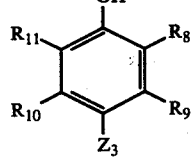

wherein $R_7$ represents a substituent usually used for a cyan coupler, for example, a carbamyl group (e.g., alkylcarbamyl, arylcarbamyl such as phenylcarbamyl, heterocyclic carbamyl such as benzothiazolylcarbamyl, etc.), a sulfamyl group (e.g., alkylsulfamyl, aryl sulfamyl such as phenylsulfamyl, heterocyclic sulfamyl, etc.), an alkoxycarbonyl group, an aryloxycarbonyl group, and the like; $R_8$ represents an alkyl group, an aryl group, a heterocyclic group, an amino group, a carbamido group (e.g., alkylcarbamido, arylcarbamido, etc.), a sulfamido group, a sulfamyl group, a carbamyl group, and the like; $R_9$, $R_{10}$, and $R_{11}$ each represents the groups as defined in $R_8$, and further each represents a hydrogen atom, a halogen atom, an alkoxy group, and the like; and $Z_3$ represents a hydrogen atom or a group capable of being released upon color development, for example, a halogen atom, a thiocyano group, a cycloimido group (e.g., maleimido, succinimido, 1,2-dicarboximido, etc.), an arylazo group, a heterocyclic azo group, and the like, as disclosed in U.S. Pat. Nos. 2,474,293, 2,521,908, 2,423,730, etc.

In order to render the coupler non-diffusible, one or more groups containing a hydrophobic residue having from 8 to 32 carbon atoms, as a ballasting group, can be introduced into the coupler molecule. The ballasting group can be bonded to the skeletal-structure of the coupler directly or through a linkage, such as an ether, carbamido, sulfamido, ureido, ester, imido, carbamoyl, or sulfamoyl bond.

Some examples of ballasting groups are described in the examples of the DIR couplers of this invention.

Examples of suitable ballasting groups are as follows:

I. Alkyl groups and alkenyl groups, e.g., $$-CH_2-CH-(C_2H_5)_2, -C_{12}H_{25}, -C_{16}H_{33}, \text{ and } C_{17}H_{33}$$

II. Alkoxyalkyl groups, such as those described in Japanese Patent Publication No. 27563/64; e.g.,

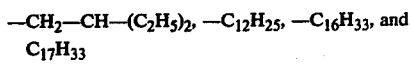

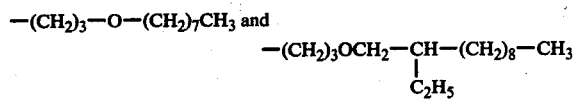

III. Alkylaryl groups, e.g.,

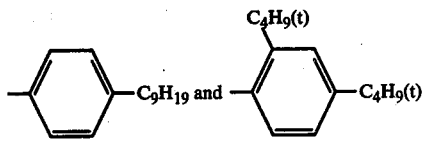

IV. Alkylaryloxyalkyl groups, e.g.,

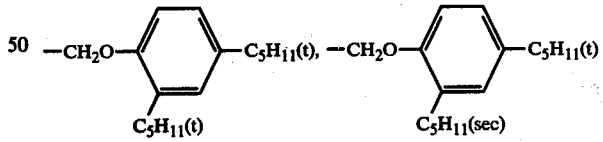

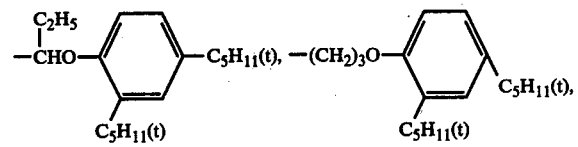

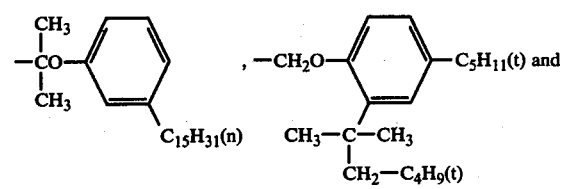

-continued

[Structure: -CH(C2H5)-O- attached to benzene ring with Cl, C5H11(t), C5H11(t) substituents]

V. Acylamidoalkyl groups, such as those described, for example, in U.S. Pat. Nos. 3,337,344 and 3,418,129; e.g., $$-CH_2CH_2N\begin{matrix}COC_{15}H_{31}\\C_4H_9\end{matrix} \text{ and}$$

$$-CH_2CH_2N\begin{matrix}COC_{13}H_{27}\\C_3H_7\end{matrix}$$

VI. Alkoxyaryl groups and aryloxyaryl groups, e.g.,

[Structure: phenyl-OC18H37(n)] and

[Structure: phenyl-O-phenyl-C12H25(n)]

VII. Groups containing both a long-chain aliphatic group such as an alkyl or alkenyl group, and a water-solubilizing group such as a carboxyl or sulfo group, e.g., $$-\underset{CH_2COOH}{CH}-CH-CH-C_{16}H_{33} \text{ and } -\underset{SO_3H}{CH}-C_{16}H_{33}$$

VIII. Alkyl groups substituted with an ester group, e.g., $$-\underset{COOC_2H_5}{CH}-C_{16}H_{33}(n) \text{ and } -CH_2-CH_2-COOC_{12}H_{25}(n)$$

IX. Alkyl groups substituted with an aryl group or a heterocyclic group, e.g., $$-CH_2-CH_2-\text{[phenyl]}-NHCOCH_2\underset{COOCH_3}{CH}-C_{18}H_{37}(n)$$

and

[Structure: -CH2CH2-phenyl-N(glutarimide with C18H37(n))]

X. Aryl groups substituted with an aryloxyalkoxycarbonyl group, e.g.,

[Structure: -phenyl-COOCH2C(CH3)2-O-phenyl with C5H11(t) and C5H11(t) substituents]

Typical examples of the couplers which can be used in this invention are described below but the invention is not to be construed as being limited to these examples.

Yellow Couplers
Y-1
α-{3-[α-(2,4-Di-tert-amylphenoxy)butyramido]benzoyl}-2-methoxyacetanilide
Y-2
α-Acetoxy-α-3-[γ-(2,4-di-tert-amylphenoxy)-butyramido]-benzoyl-2-methoxyacetanilide
Y-3
N-(4-Anisoylacetamidobenzenesulfonyl)-N-benzyl-N-toluidine
Y-4
α-(2,4-Dioxo-5,5-dimethyloxazolidinyl)-α-pivaloyl-2-chloro-5-[α-(2,4-di-tert-amylphenoxy)-butyramido]acetanilide
Y-5
α-(4-Carboxyphenoxy)-α-pivaloyl-2-chloro-5-[α-(2,4-di-tert-amylphenoxy)butyramido]acetanilide
Y-6
α-[3-(1-Benzyl-2,4-dioxo)hydantoin]-α-pivaloyl-2-chloro-5-[α-(2,4-di-tert-amylphenoxy)-butyramido]acetanilide
Y-7
α-(4-Methoxybenzoyl)-α-3.5-dioxomorpholino)-5-[γ-(2,4-di-tert-amylphenoxy)butyramido]-2-chloroacetanilide Magenta Couplers
M-8
1-(2,4,6-Trichlorophenyl)-3-[3-(2,4-di-tert-amylphenoxyacetamido)benzamido]-5-pyrazolone
M-9
1-(2,4,6-Trichlorophenyl)-3-{3-[α-2,4-di-tert-amylphenoxy)acetamido]benzamido}-4-acetoxy-5-pyrazolone
M-10
1-(2,4,6-Trichlorophenyl)-3-tridecylamido-4-(4-hydroxyphenyl)azo-5-pyrazolone
M-11
1-(2,4,6-Trichlorophenyl)-3-[(2-chloro-5-tridecanoylamino)anilino]-5-pyrazolone
M-12
1-(2,4,6-Trichlorophenyl)-3-(2-chloro-5-tetradecyloxycarbonyl)anilino-4-(1-naphthylazo)-5-pyrazolone
M-13
1-(2,4-Dichloro-6-methoxyphenyl)-3-[(2-chloro-5-tridecanoylamino)anilino]-4-benzyloxycarbonyloxy-5-pyrazolone
M-14
1-(2,4,6-Trichlorophenyl)-3-{3-[(2,4-di-tert-amylphenoxy)-acetamido]benzamido}-4-pyperidino-5-pyrazolone
M-15
1-(2,4,6-Trichlorophenyl)-3-{2-chloro-5-[α-(2,4-di-tert-amylphenoxy)butyramido]anilino}-4-N-phthalimido-5-pyrazolone
M-16

1-(2,4,6-Trichlorophenyl)-3-(chloro-5-tetradecylamino-anilino-4-(3-methyl-4-hydroxyphenylazo)-5-pyrazolone Cyan Couplers C-17
1-Hydroxy-N-[γ-(2,4-di-tert-amylphenoxypropyl)]-2-naphthamide C-18
1-Hydroxy-4-[2-(2-hexyldecyloxycarbonyl)-phenylazo]-2-[N-(1-naphthyl)]naphthamide C-19
1-Hydroxy-4-chloro-N-[γ-(2,4-di-tert-amylphenoxy)-butyl]-2-naphthamide C-20
5-Methyl-4,6-dichloro-2-[α-(3-n-pentadecylphenoxy)-butylamino]phenol C-21
1-Hydroxy-4-(2-ethoxycarbonylphenylazo)-N-(2-ethylamyl)-2-naphthamide The DIR-hydroquinone derivatives used in the present invention can be employed in combination with DIR couplers as described in U.S. Pat. Nos. 3,227,554; 3,148,062; 3,617,291; 3,733,201; 3,632,345; 3,622,328; etc., the interlayer color correction couplers (ICC couplers) as described in U.S. Pat. 3,933,500, filed Mar. 25, 1974, etc., or the organic compounds used as an interlayer interimage effect promoter. Examples of such compounds include the couplers of the following formula (VII)

$$C_p\text{-}Z_4 \quad \quad (VII)$$

wherein $C_p$ represents a coupler moiety capable of coupling with the oxidation product of a primary aromatic amine color developer; and $Z_4$ represents an organic group capable of being released on coupling with the oxidation product of an aromatic primary amine color developer and capable of, after release, diffusing and inhibiting development. $C_p$ can be selected from 4-equivalent couplers used in color light-sensitive materials; for example, a 5-pyrazolone coupler, a cyanoacetyl-coumarone coupler, an indazolone coupler, an acylacetamide coupler, a pivaloylacetamide coupler, a naphthol coupler, a phenol coupler, and the like. $Z_4$ can be a heterocyclic group forming a 1-triazole ring or a 1-diazole ring, as described in U.S. Pat. No. 3,933,500 filed Mar. 25, 1974, or the residual groups described in U.S. Pat. Nos. 3,227,554; 3,617,291; 3,622,328; 3,632,373; 3,620,745; 3,620,747; 3,615,506 and 3,617,291; British Pat. Nos. 1,201,110; 1,261,061; 1,269,075 and 1,269,073; and the like.

The DIR hydroquinone derivatives and/or the reducing compounds, particularly hydroquinone derivatives represented by general formula (II) can be used in combination with an organic interimage interlayer effect promoter compound such as those described, for example, in U.S. Pat. No. 3,892,572, U.S. Pat. No. 3,536,487; U.S. Defensive Publication T 909,022 and T 909,023; German Patent Application (OLS) Nos. 2,043,943 and 2,043,944; and the like.

Examples of these compounds are described below

ICC Uncolored Coupler

ICC-22
α-Benzoyl-α-(2-benzothiazolylthio)-4-[N-(γ-phenylpropyl)-N-(4-tolyl)sulfamyl]acetanilide ICC-23
1-{4-[γ-(2,4-Di-tert-amylphenoxy)butyramido]-phenyl}-3-piperidinyl-4-(1-phenyl-5-tetrazolylthio)-5-pyrazolone ICC-24
1-(2,4,6-Trichlorophenyl)-3-{4-[α-(2,4-di-tert-amylphenoxy)butyramido]anilino}-4-(1-phenyl-5-tetrazolylthio)-5-pyrazolone ICC-25
1-{4-[α-(2,4-Di-tert-amylphenoxy)acetamido]-phenyl}-3-methyl-4-(5- or 6-bromo-1-benztriazolyl)-5-pyrazolone ICC-26
5-Methoxy-2-[α-(3-n-pentadecylphenoxy)-butyramido]-4-(1-phenyl-5-tetrazolylthio)phenol ICC-27
N-[α-(2,4-Di-tert-amylphenoxy)acetyl]-ω-(1-phenyl-5-tetrazolylthio)-m-aminoacetophenone ICC-28
α-Pivaloyl-α-(5- or 6-bromo-1-benztriazolyl)-5-[α-(2,4-di-tert-amylphenoxy)propionamido]-2-chloroacetanilide ICC-29
α-(4-Methoxybenzoyl)-α-(5- or 6-nitro-1-benztriazolyl)-5-[γ-(2,4-di-tert-amylphenoxy)butyramido]-2-chloroacetanilide ICC-30
α-(4-Stearyloxybenzoyl)-α-(5- or 6-bromo-1-benztriazolyl)-2-methoxyacetanilide ICC-31
1-Hydroxy-4-(1-phenyltetrazolylthio)-N-[(2-chloro-5-hexadecyloxy)phenyl]-2-naphthamide Non-limiting examples of typical organic interlayer interimage effect promoter compounds are as follows:

IEPC-32
5-(3-Ethyl-2-benzothiazolylidene)-3-benzylrhodanine

IEPC-33
5-[3-(γ-Sulfopropyl)-2-benzoxazolylidene]-3-cyclohexyl-rhodanine

IEPC-34
5-(3-Methyl-2-benzoselenazolylidene)-3-(γ-sulfobutyl)-rhodanine

IEPC-35
5-[3-(β-Hydroxyethyl)-β-naphthoxazolylidene]-1-phenyl-2-thiohydantoin

IEPC-36
2-Thioxo-3-ethylbenzthiazole

IEPC-37
2-Mercapto-5-methylbenzthiazole

IEPC-38
2-Thioxo-3-n-propylbenzoxazole

IEPC-39
1,3-Di-n-propyl-2-thioxobenzimidazole

IEPC-40
N-Methyl-2-thioxo-6-chloroquinoline

The couplers used in this invention can be added in the form of a dispersion, which can be prepared in a conventional manner as has already been described in connection with the DIR hydroquinones or the compounds of general formula (II). A conventional surface active agent, such as an anionic surface active agent (e.g., sodium alkylbenzenesulfonate, sodium dioctylsulfosuccinate, sodium dodecylsulfonate, sodium alkylnaphthalenesulfonate, a Fisher coupler, etc.), an amphoteric surface active agent (e.g., N-tetradecyl-N,N-dipolyethylene-α-betaine, etc.), and an nonionic surface active agent (e.g., sorbitan monolaurate, etc.) can be employed as a dispersing agent.

The amount of the couplers used usually is from about 0.01 to 2 moles per mole of silver halide. The ICC couplers can be used alone or in combination with other couplers in an amount less than about 50 mol%, preferably less than 20 mol%, based on the total moles of the couplers used in the light-sensitive materials in accordance with the invention.

The organic interlayer interimage effect promoters are usually added in the form of a solution in water or an organic solvent miscible with water, such as methanol, ethanol, pyridine, methyl cellosolve, acetone, and the like. The amount of the promoters to be added usually is from about $10^{-7}$ to about $10^{-3}$ mole per mole of silver halide.

The silver halide grains used in the light-sensitive layers in accordance with the invention can be silver chloride or silver bromide and a mixed silver halide such as silver chlorobromide, silver iodobromide and silver chloroiodobromide, which may be monodispersed or polydispersed. The silver halide can have a wide range of mean grain sizes ranging from about 0.1 to about 3µ, depending upon the use and purposes of the photographic material. The silver halide emulsions can be prepared using, e.g., a single jet, double jet, or controlled double jet method, and can be digested by ammonia, neutral, or acid digestion method.

The silver halide emulsions used in the light-sensitive layers in accordance with the invention can be chemically sensitized using a conventional method, such as gold sensitization as described in U.S. Pat. Nos. 2,399,083; 2,597,856 and 2,597,915; reduction sensitization as described in U.S. Pat. Nos. 2,483,850 and 2,521,925; sulfur sensitization as described in U.S. Pat. Nos. 1,623,499 and 2,410,689; a sensitization using a metal ion other than silver as described in U.S. Pat. Nos. 2,448,060; 2,566,245 and 2,566,263; or a combination thereof.

The silver halide emulsions used in the present invention can also be spectrally sensitized in a conventional manner, and can contain additional additives, such as a stabilizer, e.g., a 4-hydroxy-1,3,3a,7-tetrazaindene derivative, etc., an antifogging agent, e.g., a mercapto compound, a benzothiazole derivative, etc., a coating aid, a hardener, a wetting agent, a pH-adjusting agent, e.g., citric acid, sodium carbonate, etc., and other sensitizers, e.g., an onium derivative such as the quaternary ammonium salts as described in U.S. Pat. Nos. 2,271,623; 2,288,226 and 2,334,864; and the polyalkylene oxides as described in U.S. Pat. Nos. 2,708,162; 2,531,832; 2,533,990; 3,210,191 and 3,158,484. The color photographic materials of the present invention can also contain a filter layer, a mordanting layer, and a colored layer containing a hydrophobic dye.

The light-sensitive emulsions used in the present invention can be coated on a variety of supports, such as a cellulose acetate film, a polyethylene terephthalate film, a polyethylene film, a polypropylene film, a glass plate, a baryta paper, a synthetic resin laminated paper, a synthetic paper, and the like. A suitable silver halide coating amount is about 0.1 to 20 g (as silver)/m², preferably 1 to 15 g (as silver)/m².

The color light-sensitive materials according to the present invention exposed using any type of light source, e.g., day light, tungsten light, etc., and then can be developed using a color developing solution containing a conventional p-phenylenediamine or p-aminophenol derivative as a color developing agent. Examples of suitable p-phenylene derivatives are, for example, p-amino-N-ethyl-N-β-(methansulfamidoethyl)-m-toluidine sesquisulfate monohydrate, diethylamino-p-phenylenediamine sesquisulfite, p-amino-N,N-diethyl-m-toluidine hydrochloride, p-amino-N-ethyl-N-β-hydroxyethylaniline sesquisulfate monohydrate, and the like. Other known color developing solutions can also be used which are designed for the processing of color negative materials, positive or negative color movie films, color papers, and instant color photographic materials. Examples of these color developing solutions include those described in Japanese Patent Publication No. 35749/70; Japanese Patent Application Nos. 67798/69; 13313/71 and 19516/71; H. Gordon, British J. Photo., 558 (1954); ibid., 440 (1955); ibid., 2 (1956); S. Horwitz, ibid., 212 (1960); E. Gehret, ibid., 122 (1960); ibid., 396 (1965); J. Meech, ibid., 182 (1959); German Patent Application (OLS) No. 2,238,051; and the like.

In the case of black-and-white photographic materials, a developing solution containing as a developing agent a polyhydroxybenzene, e.g., hydroquinone, pyrocatechol, pyrogallol, etc., an N-alkylaminophenol, e.g., N-methylaminophenol, N-ethylaminophenol, etc., 1-phenyl-3-pyrazolidone, e.g., 1-phenylpyrazolidone, 1-phenyl-4,4'-dimethyl-3-pyrazolidone, 1-phenyl-4,4'-dimethyl-3-pyrazolidone, etc., or a mixture thereof can be used.

The DIR hydroquinone derivatives according to the present invention can be incorporated with the reducing compounds in a light-sensitive emulsion layer, an interlayer, a filter layer, an anti-irradiation layer or a protective layer of an ordinary color light-sensitive material or an instant color light-sensitive material.

Ther term "light-sensitive emulsion layer" means a hydrophilic colloid layer containing silver halide grains having a sensitivity in a certain spectral range; a light-sensitive emulsion layer unit comprising a combination of at least two light-sensitive silver halide hydrophilic colloid layers having substantially the same spectral sensitivity and a different sensitivity, such as those described, for example, in British Pat. No. 923,045 and German Patent Application (OLS) No. 2,322,165; a light-sensitive emulsion layer unit comprising a combination of at least two light-sensitive silver halide hydrophilic colloid layers having substantially the same spectral sensitivity and a different sensitivity, and at least one non-light-sensitive hydrophilic colloid layer or a light-sensitive hydrophilic colloid layer containing silver halide grains having a sensitivity in another spectral range, separating two of the layers; and the like. For example, preferred results can be obtained by incorporating, in combination with the reducing compounds described above, the DIR hydroquinone derivatives according to the invention in a light-sensitive hydrophilic colloid layer, or an individual light-sensitive hydrophilic colloid layer or a non-light-sensitive layer contained in the light-sensitive emulsion unit.

As examples of instant light-sensitive materials which can be applied to the present invention, diffusion transfer color light-sensitive materials for producing multicolor images, such as those described Japanese Patent Publication Nos. 10240/59 and 5189/59, U.S. Pat. Nos. 2,983,606; 3,415,644; 3,415,645; 3,415,646; 3,594,164 and 3,594,165 and the like; and diffusion transfer color light-sensitive materials using DIR hydroquinones, such as those described in British Pat. No. 1,066,352 and the like are suitable.

The following evaluations demonstrate that the oxidation of the DIR hydroquinone derivatives used in the present invention can be prevented by the coexistence of a reducing compound.

A $1 \times 10^{-4}$ M solution of Compound I-38 in butyl acetate was added to a test tube, allowed to stand for 2 days at 25° C., and the percentage of the compound unchanged was measured spectrophotometrically (UV absorption). Almost all of the compound was found to be oxidized.

The percentage of unchanged DIR hydroquinone derivatives was measured in a similar manner as above, except that a reducing compound in accordance with the invention was added to the solution at a proportion of 5 mol% based on the moles of the DIR hydroquinone derivative.

Table 1

| Compound Used | Compound I-38 Unchanged (%) | Eox of the Reducing Compound Used (Volt) |
|---|---|---|
| Compound I-38 | 0 | — |
| Compound I-38 + Compound R-1 | 75 | 0.821 |
| Compound I-38 + Compound R-2 | 26 | 0.763 |
| Compound I-38 + Compound R-3 | 62 | 0.882 |
| Compound I-38 + Compound R-4 | 43 | 0.753 |
| Compound I-38 + Compound R-5 | 59 | 0.896 |
| Compound I-38 + Compound R-6 | 15 | 0.795 |
| Compound I-38 + Compound R-7 | 67 | 1.042 |
| Compound I-38 + Compound R-8 | 58 | 1.086 |
| Compound I-38 + Compound R-9 | 68 | 1.162 |
| Compound I-38 + Compound R-10 | 65 | 0.934 |

It can be seen from the results shown above that the reducing compounds according to the invention stabilize the DIR hydroquinone derivative.

The following examples are given to illustrate the present invention in greater detail. Unless otherwise indicated, all parts, percents, ratios and the like are by weight.

EXAMPLE 1

Sample 101-1 was prepared by coating, in succession, Layer 1, 2, 3, and 4 onto a piece of transparent cellulose triacetate film, as shown in FIG. 1. The coating solutions used for each layer were prepared in the following manner:

Layer 1 (red-sensitive layer):

One kilogram of a silver halide emulsion (Ag, 0.6 mole; iodine content, 6 mol%) was spectrally sensitized using $4 \times 10^{-5}$ mole of Sensitizing Dye I below. To the resulting emulsion was added (1) 450 g of Emulsion I prepared by dissolving 100 g of Coupler C-17 in 100 ml of tricresyl phosphate and 200 ml of ethyl acetate and dispersing the resulting solution into 1 Kg of a 10% gelatin aqueous solution in the presence of 4 g of sodium nonylbenzenesulfonate, and (2) an aqueous solution of 0.1 g of 2,4-dichloro-6-hydroxytriazine sodium salt.

Layer 2 (interlayer):

One hundred grams of Reducing Compound R-1 was dissolved in 100 ml of tricresyl phosphate, and the resulting solution was dispersed into 1 Kg of a 10% gelatin aqueous solution in a similar manner as in Emulsion I described above to prepare Emulsion II. To 1 Kg of a 10% gelatin aqueous solution was added 250 g of Emulsion II, and the mixture was stirred.

Layer 3 (green-sensitive layer):

One kilogram of a silver iodobromide emulsion (identical to that of Layer 1) was spectrally sensitized using $2 \times 10^{-4}$ mole of Sensitizing Dye III and $6 \times 10^{-5}$ mole of Sensitizing Dye IV as shown below. To the emulsion thus obtained was added 600 g of Emulsion III prepared by using 100 g of Coupler M-8 in a similar manner as in Layer 1.

Layer 4 (protective layer):

To 1 Kg of a 10% gelatin aqueous solution was added 0.2 g of sodium nonylbenzenesulfonate.

The sensitizing dyes used in the above preparations were as follows:

Sensitizing Dye I:
Anhydro-5,5'-dichloro-3,3'-sulfopropyl-9-ethyl-thiacarbocyanine hydroxide pyridium salt Sensitizing Dye II:
Anhydro-9-ethyl-3,3'-di-(sulfopropyl)-4,5,4',5'-dibenzocarbocyanine hydroxide ethylamine salt Sensitizing Dye III:
Anhydro-9'-ethyl-5,5'-dichloro-3,3'-disulfopropyloxacarbocyanine sodium salt Sensitizing Dye IV:
Anhydro-5,6,5',6'-tetrachloro-1,1'-diethylimidazolocarbocyanine hydroxide sodium salt Emulsion IV was obtained using 100 g of DIR Hydroquinone Compound I-38 in place of 100 g of Reducing Compounds R-1 in Layer 2 in Sample 101-1. Sample 101-2 was obtained in a similar manner as for Sample 101-1, except that 508 g of Emulsion IV was used in place of 250 g of Emulsion II and 258 g of a 10% gelatin aqueous solution obtained above.

Emulsion V was obtained using a mixture of 100 g of Compound I-38 and 7.5 g of Compound R-1 instead of 100 g of Compound R-1 in Layer 2 in Sample 101-1. Sample 101-3 was obtained in a similar manner as in Sample 101-2, except that Emulsion V was employed in place of Emulsion IV. Each emulsion was coated within 30 minutes after the addition of Emulsion IV or V.

Samples 101-1, 2, and 3 were stepwise exposed to red light, green light, or white light, and processed at 38° C. according to the following steps:

|  | Time (min.) |
|---|---|
| 1. Color Development | 3.25 |
| 2. Bleaching | 6.5 |
| 3. Washing | 3.25 |
| 4. Fixing | 6.5 |
| 5. Washing | 3.25 |
| 6. Stabilizing | 3.25 |

Each solution used in the above processing steps had the following compositions:

| Color Developing Solution | | |
|---|---|---|
| Sodium NItrilotriacetate | 1.0 | g |
| Sodium Sulfite | 4.0 | g |
| Sodium Carbonate | 30.0 | g |
| Potassium Bromide | 1.4 | g |
| Hydroxylamine Sulfate | 2.4 | g |
| 4-(N-Ethyl-N-β-hydroxylethylamino)-2-methylaniline Sulfate | 4.5 | g |
| Water to make | 1 | liter |
| Bleaching Solution | | |
| Ammonium Bromide | 160.0 | g |
| Ammonia (28% aq. soln.) | 25.0 | ml |
| Ethylenediaminetetraacetic Acid Sodium Iron Salt | 130 | g |
| Glacial Acetic Acid | 14 | ml |
| Water to make | 1 | liter |
| Fixing Solution | | |
| Sodium Tetrapolyphosphate | 2.0 | g |
| Sodium Sulfite | 4.0 | g |
| Ammonium Thiosulfate (70% aq. soln.) | 175.0 | ml |
| Sodium Bisulfite | 4.6 | g |
| Water to make | 1 | liter |
| Stabilizing Solution | | |
| Formaldehyde (38% aq. soln.) | 8.0 | ml |

| | -continued | |
|---|---|---|
| Water to make | 1 | liter |

The transmission density of the processed samples to red and green light was measured. The results obtained are shown in Table 2.

Table 2

| Sample | Light Used for Exposure | Relative Sensitivity Green-Sensitive Layer | Relative Sensitivity Red-Sensitive Layer | Gradation Green-Sensitive Layer | Gradation Red-Sensitive Layer |
|---|---|---|---|---|---|
| 101-1 | Green | 100 | — | 1.21 | — |
| | Red | — | 100 | — | 1.20 |
| | White | — | — | 1.19 | 1.17 |
| 101-2 | Green | 90 | — | 0.62 | — |
| | Red | — | 93 | — | 0.70 |
| | White | — | — | 0.55 | 0.53 |
| 101-3 | Green | 98 | — | 0.99 | — |
| | Red | — | 99 | — | 1.03 |
| | White | — | — | 0.85 | 0.80 |

As is shown by the results in Table 2, a softening of the gradation and a reduction in the sensitivity occur in contiguous layers when Compound I-38 alone was employed in the interlayer, whereas only a slight reduction in sensitivity occured and an interlayer interimage effect was exerted with respect to each other when Compound I-38 and Compound R-1 were employed in combination. The term "interlayer interimage effect" as used herein means a development effect such that development is controlled in contiguous layers depending on the amount of exposure or development in the layer. Thus, color purity is increased and color reproducibility is improved in the layers. From the results in Table 2, greater differences between the gradation in the green-sensitive layer or the red-sensitive layer to green light or red light and the gradation in the green-sensitive layer or the red-sensitive layer to white light (both the green-sensitive layer and the red-sensitive layer are exposed simultaneously) occur in Samples 101-2 and 101-3 than in Sample 101-1, respectively which indicates that the interlayer interimage effect is exerted with respect to each other between the green-sensitive layer and the red-sensitive layer.

Sample 101-1, 2, and 3 were then knife-edge exposed to soft X-rays, and processed as described above. Sample 101-2 as well as Sample 101-3 were demonstrated to have superior granularity as well to that of Sample 101-1.

EXAMPLE 2

Sample 102-1, 102-2, and 102-3 were produced as follows:

Sample 102-1:
This sample was prepared in the same manner as for Sample 101-1 in Example 1.

Sample 102-2:
This sample was prepared in the same manner as for Sample 101-2 in Example 1, except that 84 g of Compound I-2 was used in place of 100 g of Compound I-38.

Sample 102-3:
This sample was prepared in the same manner as in Sample 101-3 in Example 1, except that 91.2 g of Compound I-2 and 8.8 g of Compound R-1 were used in place of 92.5 g of Compound I-38 and 7.5 g of Compound R-1.

These samples were exposed and processed as described in Example 1, and the density of the samples was measured to red and green light. In Sample 102-2 the gradation and sensitivity in contiguous layers were reduced, whereas in Sample 102-3 DIR effects (interlayer interimage effect, edge effect) were exerted without a reduction the sensitivity in contiguous layers.

After storage for 4 days at 40° C. and 80% R.H., the samples were exposed and processed as described in Example 1, and their density was measured to red and green light. In Sample 102-2 the gradation and sensitivity in contiguous layers were significantly reduced as compared with those of Sample 102-1, whereas in Sample 102-3 the gradation and sensitivity were only slightly reduced.

EXAMPLE 3

Sample 103-1 was prepared in similar manner as in Sample 101-1 in Example 1, except that an emulsion prepared which did not contain the silver iodobromide emulsion and Sensitizing Dye I and II from Emulsion I used in Layer 1 was employed in place of Emulsion I; Sample 103-2 was prepared in the same manner as in Sample 103-1, except that an emulsion containing both Coupler C-17 (90 mol%) and Compound I-38 (10 mol%) was used in place of the emulsion of Coupler C-17 dispersed in Layer 1; Sample 103-3 was prepared in the same manner as in Sample 103-2, excepting that an emulsion containing an additional 5 mol% of Compound R-1, on a molar basis to Compound I-38, was employed in Layer 1; and Samples 103-4, 103-5, 103-6, 103-7, and 103-8 were prepared in the same manner as in Sample 103-3, except that Compounds R-4, R-5, R-7, R-9, or R-10 was used in place of Compound R-1.

Samples 103-1 to 103-8 were stepwise exposed and processed as described in Example 1. The samples were also exposed and processed as described above after storage for 4 days at 40° C. and 75% R.H.

If some of DIR hydroquinone compound, I-38, is oxidized and converted to the hydroquinone form, or some of the development inhibitor is released during emulsification, coating, or storage under high temperature and humidity conditions, the development in the contiguous layer (Layer 3) is inhibited, causing a softening in gradation and a reduction in sensitivity. The relative sensitivity and gradation were determined by measurement of the transmission density to red light. The results obtained are shown in Table 3.

Table 3

| Sample | Reducing Compound | Gamma of Layer 3 Fresh | Gamma of Layer 3 Stored | Relative Sensitivity of Layer 3 Fresh | Relative Sensitivity of Layer 3 Stored |
|---|---|---|---|---|---|
| 103-1 | (Coupler C-17 alone) | 0.81 | 0.80 | 100 | 102 |
| 103-2 | — | 0.53 | 0.46 | 88 | 85 |
| 103-3 | Compound R-1 | 0.79 | 0.77 | 99 | 100 |
| 103-4 | Compound R-4 | 0.70 | 0.70 | 97 | 96 |
| 103-5 | Compound R-5 | 0.75 | 0.72 | 98 | 98 |
| 103-6 | Compound R-7 | 0.77 | 0.71 | 100 | 99 |
| 103-7 | Compound R-9 | 0.78 | 0.78 | 101 | 99 |
| 103-8 | Compound R-10 | 0.74 | 0.67 | 97 | 98 |

Table 3 shows that the reduction of gamma and relative sensitivity in the contiguous layer (Layer 3) can be prevented using the reducing compounds in combination with the DIR hydroquinone compound, that is, the DIR hydroquinone compound, I-3, can be chemically stabilized by the reducing compounds.

EXAMPLE 4

Sample 104-1 was obtained by coating, in succession, Layer 1 and 2 onto a transparent cellulose triacetate film support. The composition and the preparation of the coating solutions used for Layer 1 and 2 were the same as those of Layer 1 and 4 in Sample 101-1 of Example 1 above, respectively. Sample 104-2 was obtained in a similar manner as in Sample 104-1, except that an emulsion containing simultaneously both Coupler C-17 (90 mol%) and Compound I-38 (10 mol%) was employed in place of the emulsion containing Coupler C-17 used in Layer 1 in Sample 104-1. Sample 104-3 was obtained in a similar manner as in Sample 104-2, except that an additional 30 mol% of Compound R-1, based on the amount of Compound I-38, was incorporated in the emulsion used in Layer 1. Sample 104-4 was obtained in a similar manner as in Sample 104-3, except that 20 mol% of Compound R-1 and 10 mol% of Compound R-9, based on the amount of Compound I-38, were used instead of using 30 mol% of Compound R-1 based on the amount of Compound I-38. Sample 104-5 was obtained in a similar manner as in Sample 104-4, excepting that 28 mol% of Compound R-1 and 2 mol% of Compound R-9, based on the amount of Compound I-38, were used instead of using 20 mol% of Compound R-1 and 10 mol% of Compound R-9 based on the amount of Compound I-38.

Samples 104-1, 104-2, 104-3, 104-4, and 104-5 were stepwise exposed to red light, knife-edge exposed to soft X-rays, and processed as shown in Example 1. The measurement of the macroscopic and microscopic density of the samples to red light showed that:

(1) in Sample 104-2 the reduction in sensitivity was much larger than that of Sample 104-1, (2) in Sample 104-3 the DIR effects (edge effect, granularity-improving effect) could be obtained with little reduction in sensitivity, and (3) in Samples 104-4 and 104-5, where two kinds of reducing compounds were employed in combination, the DIR effects could be obtained without any desensitization.

EXAMPLE 5

A multilayer light-sensitive material (Sample 105-1) was prepared by coating, as shown in FIG. 1, onto a piece of cellulose triacetate film Layer 1 to 11 having the following composition.

Layer 1 (Anti-halation Layer):
  A gelatin layer containing black colloidal silver
Layer 2 (Interlayer):
  A gelatin layer containing an emulsified dispersion of Compound R-1
Layer 3 (First red-sensitive emulsion layer):
  A silver iodobromide emulsion (iodide content, 7 mol%; average particle size, 0.4μ) layer with a silver coverage of 1.2 g/m$^2$ and containing 6 × 10$^{-5}$ mole of Sensitizing Dye I (as described in Example 1), 1.5 × 10$^{-5}$ mole of Sensitizing Dye II (as described in Example 1), 0.09 mole of Coupler C-17 (in the form of an emulsified dispersion), and 0.02 mole of Coupler C-19, per mole of silver
Layer 4 (Second red-sensitive emulsion layer):
  A silver iodobromide emulsion (iodide content, 6 mol%; average grain size, 0.8μ) layer with a silver coverage of 1.2 g/m$^2$ and containing 3 × 10$^{-5}$ mole of Sensitizing Dye I, 1.2 × 10$^{-5}$ mole of Sensitizing Dye II, 0.02 mole of Coupler C-17, and 0.04 mole of Coupler C-18, per mole of silver
Layer 5 (Interlayer):
  A gelatin layer containing an emulsified dispersion of Compound R-1
Layer 6 (First green-sensitive emulsion layer):
  A silver iodobromide emulsion (iodide content, 7 mol%; average particle size, 0.4μ) layer with a silver coverage of 1.4 g/m$^2$ and containing 3 × 10$^{-5}$ mole of Sensitizing Dye III (as described in Example 1), 1 × 10$^{-5}$ mole of Sensitizing Dye IV (as described in Example 1), 0.06 mole of Coupler M-8, and 0.015 mole of Coupler ICC-25, per mole of silver
Layer 7 (Second green-sensitive emulsion layer):
  A silver iodobromide emulsion (iodide content, 6 mol%; average grain size, 0.7μ) layer with a silver coverage of 1.5 g/m$^2$ and containing 2.5 × 10$^{-5}$ mole of Sensitizing Dye III, 0.8 × 10$^{-5}$ mole of Sensitizing Dye IV, 0.004 mole of Coupler ICC-25, and 0.013 mole of Coupler M-9, per mole of silver
Layer 8 (Yellow filter layer):
  A gelatin layer containing an emulsified dispersion of Compound R-1 and yellow colloidal silver
Layer 9 (First blue-sensitive emulsion layer):
  A silver iodobromide emulsion (iodide content, 7 mol%; average grain size, 0.4μ) layer with a silver coverage of 1.0 g/m$^2$ and containing 0.25 mole of Coupler Y-4 per mole of silver
Layer 10 (Second blue-sensitive emulsion layer):
  A silver iodobromide emulsion (iodide content, 6 mol%; average grain size, 0.8μ) layer having a silver coverage of 1.1 g/m$^2$ and containing 0.07 mole of Coupler Y-4 per mole of silver
Layer 11 (Protective layer):
  A gelatin layer containing polyethyl acrylate grains (average diameter, 1.5μ)

Each layer was coated by using, in addition to the components shown above, a gelatin hardener and a coating aid as employed in Example 1. The above emulsions were sensitized using sulfur sensitization, in advance.

Sample 105-2 was prepared in a similar manner as in Sample 105-1 above, except that 0.01 mole and 0.009 mole of Compound I-38 were incorporated in Layers 3 and 5, respectively, in the form of an emulsified dispersion (dispersing agent, tricresyl phosphate), and the coverage of silver in Layers 3 and 5 was increased to 1.5 and 1.6 g/m$^2$, respectively.

Sample 105-3 was prepared in a similar manner as in Sample 105-2, except that 0.1 mole of Compound R-1, based on the amount of Compound I-38, was incorporated in Layers 3 and 5, respectively, in the form of an emulsion containing both Compound I-38 and Compound R-1.

Samples 105-1, 105-2, and 105-3 were processed to form a 16 mm color negative light-sensitive material. After storage for 4 days at 40° C. and 80% R. H., the film was loaded in a still camera, exposed, and processed according to the steps shown in Example 1 to produce color negatives.

The color negative obtained from Sample 105-2 showed improved granularity and sharpness as compared with the granularity and sharpness of the negative from Sample 105-1, but the red- and green-sensitive layers, particularly the former, of Sample 105-2 had a tendency to be desensitized and the contrast reduced so that its color balance was disturbed. On the other hand, this desensitization and softening did not take place in Sample 105-3.

|        | Red Sensitive Layer | | Green-Sensitive Layer | | Blue-Sensitive Layer | |
|--------|----------------------|-------|---------|-------|---------|-------|
| Sample | Relative Sensitivity | Gamma | Relative Sensitivity | Gamma | Relative Sensitivity | Gamma |
| 105-1 | 100 | 0.80 | 100 | 0.81 | 100 | 0.81 |
| 105-2 | 95  | 0.71 | 96  | 0.69 | 100 | 0.80 |
| 105-3 | 99  | 0.79 | 101 | 0.80 | 99  | 0.80 |

Similar results were obtained by using Compounds R-4, R-5, R-7, or R-9 instead of Compound R-1 in Sample 105-3.

EXAMPLE 6

Sample 106-1 was prepared in the same manner as in Sample 105-1. Sample 106-2 was prepared in a similar manner as in Sample 105-1, except that Compound I-2 was used in place of Compound R-1 contained in Layer 5 (interlayer), and the coverages of silver in Layers 3, 4, 6, and 7 were altered from 1.2, 1.1, 1.4, and 1.5 g/m², respectively, to 1.3, 1.35, 1.45, and 1.55 g/m², respectively, in order to regulate the gamma of the light-sensitive layers in the sample. Sample 106-3 was prepared in a similar manner as in Sample 105-1, except that Compound I-2 (70 mol%) and Compound R-1 (30 mol%) were used in place of Compound R-1 contained in Layer 5 (interlayer), and the coverages of silver in Layers 3, 4, 6, and 7 were altered from 1.2, 1.1, 1.4, and 1.5 g/m², respectively, to 1.3, 1.35, 1.4, and 1.55, respectively, in order to regulate the gamma of the light-sensitive layers in the sample.

Samples 106-1, 106-2, and 106-3 were processed in the same manner as in Example 4 to produce color negatives. The results obtained are shown in the following Table.

|        | Red-Sensitive Layer | | Green-Sensitive Layer | | Blue-Sensitive Layer | |
|--------|----------------------|-------|---------|-------|---------|-------|
| sample | Relative Sensitivity | Gamma | Relative Sensitivity | Gamma | Relative Sensitivity | Gamma |
| 106-1 | 100 | 0.85 | 100 | 0.81 | 100 | 0.81 |
| 106-2 | 97  | 0.70 | 97  | 0.72 | 100 | 0.79 |
| 106-3 | 100 | 0.80 | 101 | 0.80 | 101 | 0.81 |

It can be clearly seen from the results in the above table that the desensitization and the softening of gradation which are caused by Compound I-2 during storage under high temperature and high humidity conditions can be prevented by the addition of the reducing compound (Compound R-1). In addition, Sample 106-3 had improved granularity, sharpness, and color reproducibility, as compared with the granularity, sharpness and color reproducibility of Samples 106-1, and 106-2.

Similar results were obtained by using Compounds R-2, R-3, R-7, or R-9 in place of Compound R-1 in Sample 106-3.

EXAMPLE 7

Sample 107-1 was prepared by coating a silver iodobromide emulsion at a coverage of silver of 3 × 10⁻² mole/m² and of gelatin of 5.5 g/m² onto a piece of cellulose triacetate film. Sample 107-2 was prepared in a similar manner as in Sample 107-1, except that Compound I-38 was dispersed using tricresyl phosphate as a dispersant, and the resulting dispersion was added to the silver iodobromide emulsion (0.03 mole of Compound I-38 was employed per mole of silver). Sample 107-3 was prepared in a similar manner as in Sample 107-2, except that a combination of Compound I-38 (70 mol%) and Compound R-1 (30 mol%) was used in place of Compound I-38.

After storage for 4 days at 40° C. and 80% R.H., Samples 107-1, 107-2, and 107-3 were stepwise exposed, and processed for 5 minutes at 20° C. in a developing solution having the following composition:

|                     | g/liter |
|---------------------|---------|
| Metol               | 0.3     |
| Sodium Sulfite      | 40.0    |
| Hydroquinone        | 6.0     |
| Sodium Carbonate    | 21.8    |
| Potassium Bromide   | 0.86    |
| Sodium Metabisulfite | 1.15   |
| Citric Acid         | 0.7     | followed by fixing in a fixing solution having the following composition, washing, and drying.

|                           |        |
|---------------------------|--------|
| Sodium Thiosulfate (anhydrous) | 153.0 g |
| Sodium Sulfite (anhydrous) | 150.0 g |
| Glacial Acetic Acid       | 13.5 ml |
| Boric Acid                | 7.5 g  |
| Potassium Alum            | 15.0 g |
| Water to make             | 1 liter |

The results obtained from the measurement of the density are shown in the following table.

| Sample | Relative Sensitivity | Gamma | Fog  |
|--------|----------------------|-------|------|
| 107-1  | 100 | 3.08 | 0.06 |
| 107-2  | 90  | 2.10 | 0.04 |
| 107-3  | 98  | 2.31 | 0.05 |

As is clearly shown by the results in the table above, desensitization occurs with Sample 107-2, which contains Compound I-38 alone, whereas a softening of gradation can be attained without desensitization in Sample 107-3, which contains Compound I-38 and Compound R-1 in combination. On the other hand, Sample 107-3 also had improved granularity.

Similar results were obtained using Compounds R-2, R-3, R-5, R-8, or R-9 in place of Compound R-1, or by using Compounds I-2, or I-10 in place of Compound I-38.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive material comprising at least one hydrophilic colloid layer containing a dispersion containing at least one reducing compound having an oxidation potential of from about 0.5 to 1.5 volts and at least one compound represented by the following general formula (I):

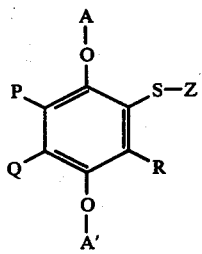

(I)

a compound represented by the following general formula (II):

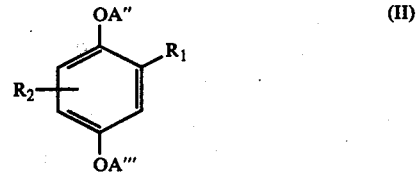

wherein A and A' which may be the same or different, each represents a hydrogen atom or an alkaline-hydrolyzable group, or A' may combine with R or Q to form a ring; P, Q, and R, which may be the same or different, each represents a hydrogen atom, an alkyl group, an aryl group, a halogen atom, a hydroxyl group, a —Y—W group wherein Y represents an oxygen atom or a sulfur atom, and W represents an alkyl group, an aryl group, or a heterocyclic group; wherein Z represents a heterocyclic group which is substantially photographically inert in the bonded state; with at least one ballasting group having at least 5 carbon atoms being contained in said molecule.

2. The photographic light-sensitive material as claimed in claim 1, wherein said reducing compound has an oxidation potential of from 0.7 to 1.2 volts.

3. The photographic light-sensitive material as claimed in claim 1, wherein said reducing compound is selected from the group of 2,5-di-tert-octylhydroquinone, 2-n-octadecylthiohydroquinone, 2-n-hexadecylhydroquinone, 2-n-octadecylthio-5-tert-octylhydroquinone, hydroquinone, 2-(3'-methylphenyl)hydroquinone and 2,3,5-trimethylhydroquinone.

4. The photographic light-sensitive material as claimed in claim 1, wherein said reducing compound is selected from the group of ascorbic acid and ascorbic palmitate.

5. The photographic light-sensitive material as claimed in claim 1, wherein said reducing compound is 7,7'-dimethyl-6,6'-dihydroxy-4,4,4',4'-tetramethylbis-2,2'-spirochroman.

6. The photographic light-sensitive material as claimed in claim 1, wherein said reducing compound is hydroxylamine.

7. The photographic light-sensitive material as claimed in claim 1, wherein said reducing compound is pyrogallol.

8. The photographic light-sensitive material as claimed in claim 1, wherein A and A' represent a hydrogen atom.

9. The photographic light-sensitive material as claimed in claim 8, wherein said compound represented by the general formula (I) has the general formula (Ib)

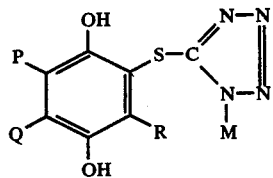

wherein P, Q, and R each are as defined in claim 5, and M represents a phenyl group or a lower alkyl group.

10. The photographic light-sensitive material as claimed in claim 1, wherein said reducing compound is a compound represented by the following general formula (II):

(II)

wherein $R_1$ and $R_2$ each represents a hydrogen atom or a straight-chain or branched alkyl group containing from 8 to 20 carbon atoms; and A'' and A''' each represents a hydrogen atom or an alkaline hydrolyzable group.

11. The photographic light-sensitive material as claimed in claim 10, wherein said reducing compound is soluble in water.

12. The photographic light-sensitive material as claimed in claim 10, wherein said reducing compound is present in a proportion of from about 1 mol% to about 70 mol%, based on the total moles of the reducing compound and the compound represented by general formula (I).

13. The photographic light-sensitive material as claimed in claim 12, wherein said reducing compound is present at a proportion of from 10 mol% to 60 mol%, based on the total moles of the reducing compound and the compound represented by general formula (I).

14. The photographic light-sensitive material as claimed in claim 1, wherein said hydrophilic colloid layer is a non-light-sensitive emulsion layer and contains a dispersion prepared by dispersing in a hydrophilic colloid a solution containing at least one reducing compound and at least one compound represented by general formula (I).

15. A process for producing a photographic light-sensitive material comprising at least one hydrophilic colloid layer containing a dispersion containing at least one reducing compound having an oxidation potential of from about 0.5 to 1.5 volts and at least one compound represented by the following general formula (I):

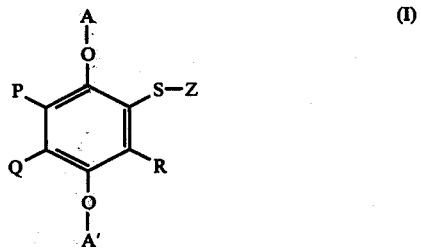

(I)

wherein A and A' which may be the same or different, each represents a hydrogen atom or an alkaline-hydrolyzable group, or A' may combine with R or Q to form a ring; P, Q, and R, which may be the same or different, each represents a hydrogen atom, an alkyl group, an aryl group, a halogen atom, a hydroxyl group, a —Y—W group wherein Y represents an oxygen atom or a sulfur atom, and W represents an alkyl group, an aryl group, or a heterocyclic group; wherein Z represents a heterocyclic group which is substantially photographically inert in the bonded state with at least one ballasting group having at least 5 carbon atoms being contained in said molecule, said process comprising dissolving at least one reducing compound and at least one compound represented by general formula (I) in an organic solvent, and dispersing the solution into a hydrophilic colloid solution.

16. A process for producing a silver halide photographic light-sensitive material comprising at least one hydrophilic colloid layer containing a dispersion containing at least one reducing compound and at least one compound represented by the following general formula (I):

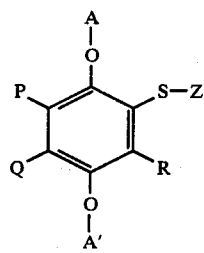

wherein A and A' which may be the same or different, each represents a hydrogen atom or an alkaline-hydrolyzable group, or A' may combine with R or Q to form a ring; P, Q, and R, which may be the same or different, each represents a hydrogen atom, an alkyl group, an aryl group, a halogen atom, a hydroxyl group, a —Y—W group wherein Y represents an oxygen atom or a sulfur atom, and W represents an alkyl group, an aryl group, or a heterocyclic group; wherein Z represents a heterocyclic group which is substantially photographically inert in the bonded state; with at least one ballasting group having at least 5 carbon atoms being contained in said molecule, said process comprising dissolving at least one reducing compound and at least one compound represented by general formula (I) in an organic solvent, dispersing the solution into a hydrophilic colloid, incorporating the dispersion into a coating solution for a hydrophilic colloid emulsion, and coating the resulting coating solution on a support substantially immediately after the incorporation of said dispersion.

17. A photographic light-sensitive material comprising a support having thereon at least one hydrophilic colloid layer containing a dispersion containing at least one reducing compound having an oxidation potential of from about 0.5 to 1.5 volts and at least one compound represented by the following general formula (I):

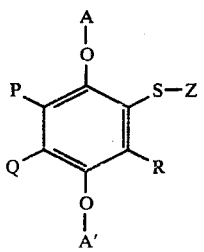

wherein A and A', which may be the same or different, each represents a hydrogen atom or an alkaline-hydrolyzable group, or A' may combine with R or Q to form a ring; P, Q, and R, which may be the same or different, each represents a hydrogen atom, an alkyl group, an aryl group, a halogen atom, a hydroxyl group, a —Y—W group wherein Y represents an oxygen atom or a sulfur atom, and W represents an alkyl group, an aryl group, or a heterocyclic group; wherein Z represents a heterocyclic group which is substantially photographically inert in the bonded state; with at least one ballasting group having at least 5 carbon atoms being contained in said molecule.

18. A multi-layer color photographic light-sensitive material comprising a support having thereon a blue-sensitive silver halide emulsion layer unit containing a yellow coupler, a green-sensitive silver halide emulsion layer unit containing a magenta coupler, and a red-sensitive silver halide emulsion layer unit containing a cyan coupler, with at least one compound represented by general formula (I):

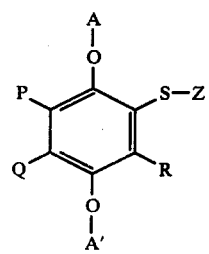

wherein A and A' each represents a hydrogen atom or an alkaline-hydrolyzable group, or A' may combine with R or Q to form a ring; and P, Q, and R each represents a hydrogen atom, an alkyl group, a halogen atom, a hydroxyl group, a —Y—W group, wherein Y represents an oxygen atom or a sulfur atom and W represents an alkyl group, an aryl group or a heterocyclic group; wherein Z represents a heterocyclic group which is substantially photographically inert in the bonded state; with at least one ballasting group having at least 5 carbon atoms being contained in the molecule, and at least one reducing compound having an oxidation potential of from about 0.5 to 1.5 volts being contained in a dispersion in at least one of the silver halide emulsion layers or an interlayer of said units.

19. The multi-layer color photographic light-sensitive material as claimed in claim 18, wherein at least one of said units contains two or more emulsion layers.

20. A photographic light-sensitive material having at least one hydrophilic colloid layer produced by dissolving in an organic solvent at least one reducing compound having an oxidation potential of from about 0.5 to 1.5 volts and at least one compound represented by the following general formula (I):

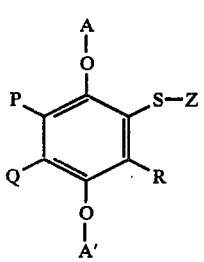

wherein A and A' which may be the same or different, each represents a hydrogen atom or an alkaline-hydrolyzable group, or A' may combine with R or Q to form a ring; P, Q, and R, which may be the same or different, each represents a hydrogen atom, an alkyl group, an aryl group, a halogen atom, a hydroxyl group, a —Y—W group wherein Y represents an oxygen atom or a sulfur atom, and W represents an alkyl group, an aryl group, or a heterocyclic group; wherein Z represents a heterocyclic group which is substantially photographically inert in the bonded state; with at least one ballasting group having at least 5 carbon atoms being contained in said molecule, and dispersing said solution into said hydrophilic colloid layer.

21. A photographic light-sensitive material having at least one hydrophilic colloid layer produced by dissolving in an organic solvent at least one reducing compound having an oxidation potential of from about 0.5 to 1.5 volts and at least one compound represented by the following general formula (I):

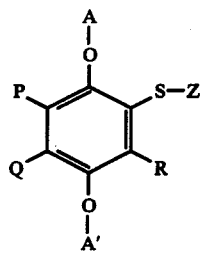

(I)

wherein A and A' which may be the same or different, each represents a hydrogen atom or an alkaline-hydrolyzable group, or A' may combine with R or Q to form a ring; P, Q, and R, which may be the same or different, each represents a hydrogen atom, an alkyl group, an aryl group, a halogen atom, a hydroxyl group, a —Y—W group wherein Y represents an oxygen atom or a sulfur atom, and W represents an alkyl group, an aryl group, or a heterocyclic group; wherein Z represents a heterocyclic group which is substantially photographically inert in the bonded state, with at least one ballasting group having at least 5 carbon atoms being contained in said molecule, dispersing said solution into a hydrophilic colloid material incorporating the dispersion into a coating solution for a hydrophilic colloid emulsion, and coating the resulting coating solution on a support immediately after the incorporation of said dispersion.

22. A photographic light-sensitive material having at least one hydrophilic colloid layer produced by placing in said layer a dispersion containing at least one reducing compound having an oxidation potential of from about 0.5 to 1.5 volts and at least one compound represented by the following general formula (I):

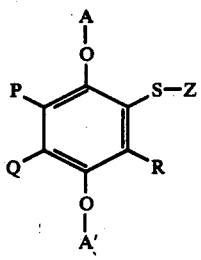

(I)

wherein A and A' which may be the same or different, each represents a hydrogen atom or an alkaline-hydrolyzable group, or A' may combine with R or Q to form a ring; P, Q, and R, which may be the same or different, each represents a hydrogen atom, an alkyl group, an aryl group, a halogen atom, a hydroxyl group, a —Y—W group wherein Y represents an oxygen atom or a sulfur atom, and W represents an alkyl group, an aryl group, or a heterocyclic group, wherein Z represents a heterocyclic group which is substantially photographically inert in the bonded state; with at least one ballasting group having at least 5 carbon atoms being contained in said molecule.

23. The photographic light-sensitive material as claimed in claim 22, wherein said reducing compound has an oxidation potential of from 0.7 to 1.2 volts.

24. The photographic light-sensitive material as claimed in claim 22, wherein A and A' represent a hydrogen atom and said reducing compound has an oxidation potential less than about 1.5 volts.

25. The photographic light-sensitive material as claimed in claim 22, wherein said compound represented by the general formula (I) has the general formula (Ib)

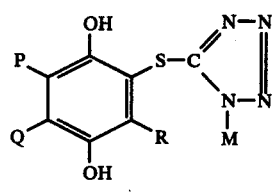

(Ib)

wherein P, Q, and R each are as defined in claim 5, and M represents a phenyl group or a lower alkyl group.

26. The photographic light-sensitive material as claimed in claim 22, wherein said reducing compound is a compound represented by the following general formula (II):

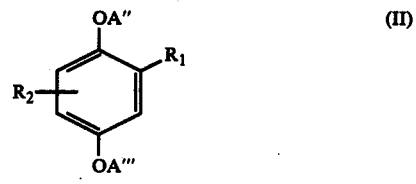

(II)

wherein $R_1$ and $R_2$ each represents a hydrogen atom or a straight-chain or branched alkyl group containing from 8 to 20 carbon atoms; A" and A'" each represents a hydrogen atom or an alkaline hydrolyzable group; and the benzene ring may be further substituted with an alkyl group containing not more than 8 carbon atoms, a halogen atom, an aryl group, a hydroxyl group, or a heterocyclic group.

27. The photographic light-sensitive material as claimed in claim 22, wherein said reducing compound is soulble in water.

28. The photographic light-sensitive material as claimed in claim 22, wherein said reducing compound is present in a proportion of from about 1 mol% to about 70 mol%, based on the total moles of the reducing compound an the compound represented by general formula (I).

29. The photographic light-sensitive material as claimed in claim 22, wherein said reducing compound is present at a proportion of from 10 mol% to 60 mol%, based on the total moles of the reducing compound and the compound represented by general formula (I).

* * * * *

UNITED STATES PATENT AND TRADEMARK OFFICE
CERTIFICATE OF CORRECTION

PATENT NO. : 4,144,071
DATED : March 13, 1979
INVENTOR(S) : Keisuke SHIBA et al

It is certified that error appears in the above-identified patent and that said Letters Patent are hereby corrected as shown below:

IN THE HEADING:

Insert -- Foreign Application Priority Data --
-- Apr. 8, 1974   Japan ....... 49-39662

Signed and Sealed this

Twenty-ninth Day of May 1979

[SEAL]

Attest:

RUTH C. MASON
Attesting Officer

DONALD W. BANNER
Commissioner of Patents and Trademarks